US011574561B2

(12) United States Patent
Sainsbury et al.

(10) Patent No.: US 11,574,561 B2
(45) Date of Patent: Feb. 7, 2023

(54) VIRTUAL REALITY SURGICAL SYSTEM INCLUDING A SURGICAL TOOL ASSEMBLY WITH HAPTIC FEEDBACK

(71) Applicant: Marion Surgical Inc., Oakville (CA)

(72) Inventors: Benjamin Sainsbury, Oakville (CA); Jessica Henry, Oakville (CA); Mihail Filippov, Etobicoke (CA); Ryan La, Aurora (CA)

(73) Assignee: Marion Surgical, Oakville (CA)

( * ) Notice: Subject to any disclaimer, the term of this patent is extended or adjusted under 35 U.S.C. 154(b) by 829 days.

(21) Appl. No.: 16/415,627

(22) Filed: May 17, 2019

(65) Prior Publication Data

US 2019/0355278 A1     Nov. 21, 2019

Related U.S. Application Data

(60) Provisional application No. 62/673,652, filed on May 18, 2018.

(51) Int. Cl.
    *G09B 23/28*          (2006.01)
    *A61B 34/00*          (2016.01)
    (Continued)

(52) U.S. Cl.
    CPC ............. *G09B 23/28* (2013.01); *A61B 34/76* (2016.02); *G06F 3/011* (2013.01); *G06F 3/016* (2013.01);
    (Continued)

(58) Field of Classification Search
    CPC ............ A61B 1/307; A61B 2034/2055; A61B 2034/2059; A61B 2034/301;
    (Continued)

(56) References Cited

U.S. PATENT DOCUMENTS 5,805,140 A    9/1998   Rosenberg et al.
7,493,153 B2   2/2009   Ahmed et al.
(Continued)

FOREIGN PATENT DOCUMENTS

CA      2144505 A1    9/1996
CA      2445017 A1    1/2001
(Continued)

OTHER PUBLICATIONS

Chen et al., "Virtual-Reality Simulator System for Double Interventional Cardiac Catheterization Using Fractional-Order Vascular Access Tracker and Haptic Force Producer," The Scientific World Journal, vol. 2015, Article ID 697569 pp. 1-12, 2015.
(Continued)

*Primary Examiner* — Insa Sadio
(74) *Attorney, Agent, or Firm* — Tony Orsi; Bereskin & Parr LLP / S.E.N.C.R.L,s.r.l.

(57) ABSTRACT

Virtual reality (VR) surgical systems with haptic feedback are described herein that can be used to simulate several instruments and surgeries. The instruments can include a tool assembly; first and second brackets each having first shafts that are rotatably coupled at first and second end regions of the tool assembly and second shafts that are rotatably coupled to first and second robotic arms; a surgical tool assembly coupled to an end portion of the tool assembly and having an elongated member that extends within the tool assembly; an elongated member position sensor assembly configured to provide position information of a position of the elongated member to a computing unit; and an elongated member force feedback assembly housed within the cavity and coupled to the elongated member. The elongated member force feedback assembly is configured to provide haptic feedback to the user of the instrument.

25 Claims, 20 Drawing Sheets

(51) Int. Cl.
  *G06F 3/01* (2006.01)
  *G06F 3/16* (2006.01)
  *A61B 34/30* (2016.01)
  *A61B 34/20* (2016.01)
  *A61B 1/307* (2006.01)

(52) U.S. Cl.
  CPC .............. *G06F 3/167* (2013.01); *A61B 1/307* (2013.01); *A61B 2034/2055* (2016.02); *A61B 2034/2059* (2016.02); *A61B 2034/301* (2016.02)

(58) Field of Classification Search
  CPC ........ A61B 2090/365; A61B 2090/368; A61B 2090/372; A61B 34/30; A61B 34/76; G06F 3/011; G06F 3/016; G06F 3/167; G09B 23/28; G09B 23/285
  See application file for complete search history.

(56) References Cited

U.S. PATENT DOCUMENTS

| | | | |
|---|---|---|---|
| 7,815,436 | B2 | 10/2010 | Cunningham et al. |
| 8,550,821 | B2 | 10/2013 | Illana Alejandro et al. |
| 9,563,266 | B2 | 2/2017 | Banerjee et al. |
| 9,700,292 | B2 | 7/2017 | Nawana et al. |
| 11,062,624 | B2 | 7/2021 | Savitzky et al. |
| 2007/0156019 | A1* | 7/2007 | Larkin .................... A61B 1/009 600/104 |
| 2009/0253109 | A1* | 10/2009 | Anvari .................... G09B 23/28 434/262 |
| 2014/0088941 | A1 | 3/2014 | Banerjee et al. |

FOREIGN PATENT DOCUMENTS

| | | |
|---|---|---|
| CA | 2648713 A1 | 11/2007 |
| CA | 2484586 C | 6/2011 |
| CA | 2914695 A1 | 12/2014 |
| CA | 2961874 A1 | 3/2017 |
| CA | 2961882 A1 | 3/2017 |
| CA | 2921848 C | 7/2017 |
| KR | 1020130128673 A | 11/2013 |
| WO | 2014/142770 A1 | 9/2014 |

OTHER PUBLICATIONS

McNamara, "Voice coil actuation technology for medical devices," AspenCore, Inc., Posted Jul. 12, 2016, 6 pages <https://www.electronicproducts.com/Sensors_and_Transducers/Transducers/Voice_coil_actuation_technology_for_medical_devices.aspx>.

Marayanan et al., "SIMBiopsies: An Augmented Reality Training SIMulator for Needle Biopsies," Conference Paper, Jun. 2011, Buffalo, United States, 2 pages.

Lee et al., "Kinematics Analysis of In-Parallel 5 DOF Haptic Device," 2010 IEEE/ASME International Conference on Advanced Intelligent Mechatronics, Jul. 6-9, 2010, Montreal, Quebec, Canada, pp. 237-241.

"Vist®-Lab Solution", brochure, Mentice AB, 2015, 2 pages <http://www.mentice.com/hubfs/_Product_Sheets/Mentice-VIST-Lab-Ir.pdf?t-1443013046460>.

"Vist® G5 Simulator", brochure, Mentice AB, 2015, 2 pages <https://cdn2.hubspot.net/hubfs/526782/_Product_Sheets/Mentice-VIST-G5-2015.pdf>.

"Vist®-C Simulator", brochure, Mentice AB, 2015, 3 pages.

"Voxel-Man Tempo," Voxel-Man Group, 2018, 4 pages. Last accessed Apr. 13, 2018. <https://www.voxel-man.com/simulator/tempo>.

"Voxel-Man Sinus," Voxel-Man Group, 2018, 3 pages. Last accessed Apr. 13, 2018 <https://www.voxel-man.com/simulator/sinus>.

Mentice, "Vist-Lab With Vist G5—Cathlab Training Setup," Mentice AB, Sweden, 2018, 5 pages. Last accessed Apr. 13, 2018. <https://www.mentice.com/vist-lab-with-vist-g5>.

Mentice, "Vist® G5 Simulator," Mentice AB, Sweden, 2018, 6 pages. Last accessed Apr. 13, 2018. <https://www.mentice.com/vist-g5>.

Virtamed, "VirtaMed ArthroS™," VirtaMed AG, Switzerland, 2018, 16 pages. Last accessed Apr. 12, 2018. <https://www.virtamed.com/en/medical-training-simulators/arthros/_hstc=753710.bc64465e64043e1554739284f988c3f1.1571256458498.1571256458498.1571256458498.1&_hssc=7537101.1571256458499&_hsfp=1639594146>.

3D Systems, "URO Mentor™—Changing the Face of Endourology Training," Simbionix USA Corporation., USA, 2017, 2 pages. Last accessed Apr. 13, 2018. <https://simbionix.com/simulators/uro-mentor>.

3D Systems, "TURP Mentor—The Most Advanced Training Simulator for TURP, TURB, and Laser BPH Treatment," Simbionix USA Corporation., USA, 2017, 2 pages. Last accessed Apr. 13, 2018. <https://simbionix.com/simulators/turp-mentor>.

Touch of Life Technologies, "ArthroSim Arthroscopy Simulator—Virtual Patients, Real Experience," Touch of Life Technoligies Inc., 2015, 2 pages. Last accessed Apr. 12, 2018. <http://www.toltech.net/medical-simulators/products/arthrosim-arthroscopy-simulator>.

Shi et al., "Three-dimensional virtual reality simulation of periarticular tumors using Dextroscope reconstruction and simulated surgery: a preliminary 10 case study," Acta Orthopaedica Belgica, China, Mar. 2014, 80(1): 132-8.

3D Systems, "Simulators," Simbionix USA Corporation., USA, 2017, 2 pages. Last accessed Apr. 12, 2018 <https://simbionix.com/simulators>.

3D Systems, "Procedure Rehearsal Studio," Simbionix USA Corporation., USA, 2017, 1 page. Last accessed Apr. 12, 2018. <https://simbionix.com/clinical-rehearsal/procedure-rehearsal-studio/>.

Limbs & Things, "Medical Training Models," Limbs & Things Ltd, USA, 2016, 7 pages. Last accessed Apr. 12, 2018. (web archive: <https://web.archive.org/web/20180412055517/https://www.limbsandthings.com/us/>).

3D Systems, "Lap Mentor™," Simbionix USA Corporation., USA, 2017, 3 pages. Last accessed Apr. 13, 2018. <https://simbionix.com/simulators/lap-mentor>.

3D Systems, "HYST Mentor," Simbionix USA Corporation., USA, 2017, 2 pages. Last accessed Apr. 13, 2018. <https://simbionix.com/simulators/hyst-mentor>.

3D Systems, "GI Mentor™—Offering the most Comprehensive Hands-On-Training for GI Procedures," Simbionix USA Corporation., USA, 2017, 1 page. Last accessed Apr. 13, 2018. <https://simbionix.com/simulators/gi-mentor>.

3D Systems, "Clinical Planning," Simbionix USA Corporation., USA, 2017, 3 pages. Last accessed Apr. 12, 2018 <https://simbionix.com/clinical-rehearsal/procedure-rehearsal-studio/clinical-planning>.

CAE Healthcare, "CAE EndoVR—Endoscopy training solution with performance feedback," CAE Healthcare, 2017, 7 pages. Last accessed Apr. 13, 2018 <https://caehealthcare.com/surgical-simulation/endovr/>.

CAE Healthcare, "CAE LapVR—Immersive, Risk-Free Laparoscopic Training Environment," CAE Healthcare, 2017, 6 pages. Last accessed Apr. 13, 2018. <https://caehealthcare.com/surgical-simulation/lapvr/>.

CAE Healthcare, "CAE CathLabVR—Risk-Free Practice of Cardiac and Peripheral Vascular Procedures," CAE Healthcare, 2017, 5 pages. Last accessed Apr. 13, 2018 <https://caehealthcare.com/surgical-simulation/cathlabvr/>.

3D Systems, "Bronch Mentor—Enhancing Bronchoscopy Training to the Full Extent of the Actual Procedure," Simbionix USA Corporation., USA, 2017, 3 pages. Last accessed Apr. 13, 2018. <https://simbionix.com/simulators/bronch-mentor>.

3D Systems, "Arthro Mentor™," Simbionix USA Corporation., USA, 2017, 3 pages. Last accessed Apr. 12, 2018 <https://simbionix.com/simulators/arthro-mentor/>.

Johnston III et al., "Video Analysis of Surgeons Performing Robot-Assisted Radical Prostatectomy: is there a Relationship between the Time Taken to Complete the Urethrovesical Anastomosis with Technical Skill?," The Journal of Urology, May 18, 2018, 199(4S): e5.

(56) References Cited

OTHER PUBLICATIONS

Goldenberg et al., "MP01-10 Content Validity Evidence for a Novel Mixed Reality Percutaneous Nephrolithotomy Simulator", The Journal of Urology, 2018, 199(4): e5-e6.

Larcher et al., "Virtual Reality-Based Validation of the ERUS Certified Training Programs Intensive Simulation Module: Results from a High-Volume Robotic Surgery Training Centre," The Journal of Urology, May 18, 2018, 199 (4S): e6.

"Rotary encoder", Wikipedia, Apr. 25, 2018 <http://web.archive.org/web/20180510163710/https://en.wikipedia.org/wiki/Rotary_encoder> (10 pages).

"VirtaMed PelvicSim™", CAE Healthcare, online product description, 2015, 3 pages <http://web.archive.org/web/20151018151407/http://www.caehealthcare.com/eng/interventional-simulators/virtamed-pelvicsim>.

Eslahpazir et al., "Principal considerations for the contemporary high-fidelity endovascular simulator design used in training and evaluation", Journal of Vascular Surgery, 2014, 59(4): 1154-1162.

"LapSim® Laparoscopic Trainer", Limbs & Things Ltd., online product description, 2015, 4 pages <http://web.archive.org/web/20150627041440/http://limbsandthings.com/uk/products/lapsim-laparoscopic-trainer>.

"LapSim®: The Proven Training System", Surgical Science Inc., online product description, 2015, 12 pages <http://web.archive.org/web/20151023031600/http://www.surgical-science.com/lapsim-the-proven-training-system>.

"EndoSim—Putting Vision into Practice", Surgical Science Inc., online product description, 2015, 6 pages <http://web.archive.org/web/20151023031556/http://www.surgical-science.com/endosim-endoscopy-simulator>.

"PROcedure Rehearsal Studio", Product Brochure, Simbionix USA Corporation, 2015, 4 pages <http://web.archive.org/web/20150906043842/http://simbionix.com/wp-content/pdf/Brochures/PROcedure_Brochure_04-2015_Web.pdf>.

"ANGIO Mentor™", Product Brochure, Simbionix USA Corporation, 2015, 6 pages <http://web.archive.org/web/20150909180228/http://simbionix.com/wp-content/pdf/Brochures/ANGIO_Mentor_Brochure_07_2015_Web.pdf>.

"BRONCH Mentor™", 3D Systems Corporation, Product Brochure, 2015 <http://simbionix.com/wp-content/pdf/Brochures/BRONCH_Mentor_Brochure_04_2015_Web.pdf> (4 pages).

"GI Mentor™", 3D Systems Corporation, Product Brochure, 2015 <http://simbionix.com/wp-content/pdf/Brochures/GI_Mentor_Brochure_06_2015-Web.pdf> (4 pages).

"LAP Mentor™", 3D Systems Corporation, Product Brochure, 2015 <http://simbionix.com/wp-content/pdf/Brochures/LAP_Mentor_Brochure_07_2015-Web.pdf> (6 pages).

"Pelvic Mentor™", Simbionix USA Corporation, Product Brochure, 2013 <http://simbionix.com/wp-content/pdf/Brochures/PELVIC_Mentor_Brochure10_2013-web.pdf> (4 pages).

URO/PERC Mentor™, Simbionix USA Corporation, Product Brochure, 2013 <http://simbionix.com/wp-content/pdf/3rochures/URO_PERCMentor02-2013-WEB.pdf> (4 pages).

"Perc Mentor™", Simbionix USA Corporation, online product description, Accessed in 2015, 1 page <http://web.archive.org/web/20150906092510/http://simbionix.com/simulators/perc-mentor>.

Ukets, "Mentice VIST-Lab—Intro and Starting the Simulator", 2013, <https://www.youtube.com/watch?V=shqklwgi7MM> (1 page).

"Robotix Mentor™", Simbionix USA Corporation, online product description, Accessed in 2015, 2 pages <http://web.archive.org/web/20150906023218/http://simbionix.com/simulators/robotix-mentor>.

"RobotiX Mentor™", 3D Systems Corporation, Product Brochure, 2015 <http://simbionix.com/wp-content/pdf/Brochures/Robotix_06_2015_Web.pdf> (4 pages).

"HYST Mentor™ TURP Mentor™", 3D Systems Corporation, Product Brochure, 2015 <http://simbionix.com/wp-content/pdf/Brochures/HYST_TURPMentor_01_2015-Web.pdf> (4 pages).

"VirtaMed PelvicSim™", CAE Healthcare and VirtaMed AG, 2015, 2 pages <http://web.archive.org/web/20151020032234/http://www.caehealthcare.com/limages/uploads/documents/VirtaMed_PelvicSim_Factsheet_141209_CAE.pdf>.

Basdogan et al., "Virtual Environments for Medical Training: Graphical and Haptic Simulation of Laparoscopic Common Bile Duct Exploration", IEEE Trans on Mechatronics, 2001, 6(3):269-285.

Morris et al., "Haptic Feedback Enhances Force Skill Learning" Second Joint EuroHaptics Conference and Symposium on Haptic Interfaces for Virtual Environment and Teleoperator Systems (WHC'07), IEEE, 2007, Tsukuba, Japan, pp. 21-26.

Williams et al., "Implementation and Evaluation of a Haptic Playback System", Haptics-e, 2004, 3(3): 1-6.

"Interventional Simulators—VirtaMed UroSim™", CAE Healthcare, Inc., webpage, 2016 <https://web.archive.org/web/20161229151432/http://www.caehealthcare.com/eng/interventional-simulators/virtamed-urosim> (3 pages).

Rossa et al., "Design and Control of a Dual Unidirectional Brake Hybrid Actuation System for Haptic Devices", IEEE Transactions on Haptics, 2014, 7(4): 442-453.

"VirtaMed HystSim™—Virtual reality training simulator for hysteroscopy", CAE Healthcare, Inc., VirtaMed AG, fact sheet, 2015 <https://web.archive.org/web/20151019075645/http://www.caehealthcare.com//images/uploads/Jocuments/VirtaMed_HystSim_Factsheet_140718_CAE.pdf> (2 pages).

"Interventional Simulators—VirtaMed HystSim™", CAE Healthcare, Inc., webpage, 2016 <https://web.archive.org/web/20170105002611/http://www.caehealthcare.com/eng/interventional-simulators/virtamed-hystsim> (3 pages).

"EndoVR™ Interventional Simulator", CAE Healthcare, Inc., brochure, 2014 <https://web.archive.org/web/20160419141350/http://caehealthcare.com//images/uploads/brochures/EndoVR.pdf> (2 pages).

"Interventional Simulators—EndoVR", CAE Healthcare, Inc., webpage, 2016 <https://web.archive.org/web/20170104224547/http://www.caehealthcare.com/eng/interventional-simulators/endovr> (4 pages).

"LapVR™ Surgical Simulator", CAE Healthcare, Inc., brochure, 2014 <https://web.archive.org/web/20160419084525/http://caehealthcare.com//images/uploads/brochures/LAPVR.pdf> (2 pages).

"Interventional Simulators—LapVR", CAE Healthcare, Inc., webpage, 2016 <https://web.archive.org/web/20170104224603/http://www.caehealthcare.com/eng/interventional-simulators/LAPVR.pdf> (4 pages).

"CathLabVR™ Interventional Simulator", CAE Healthcare, Inc., brochure, 2014 <https://web.archive.org/web/20151019133538/http://www.caehealthcare.com/images/uploads/brochures/CathLabVR.pdf> (2 pages).

"Interventional Simulators—CathLabVR", CAE Healthcare, Inc., webpage, 2016 <https://web.archive.org/web/20170120022345/http://www.caehealthcare.com/eng/interventional-simulators/cathlabVR.pdf> (3 pages).

International Search Report and Written Opinion dated Aug. 6, 2019 in International Patent Application No. PCT/CA2019/050675 (7 pages).

"VirtaMed UroSim™—Virtual reality training simulator for urology", CAE Healthcare, Inc., fact sheet, 2015 <https://web.archive.org/web/20151019091112/http://www.caehealthcare.com//images/uploads/documents/Factsheet-VirtaMed-UroSim.pdf> (2 pages).

eeNews Europe, "Haptic knob leverages magnetorheological fluids for crisp force-feedback", online article, 2018 <https://goo.gl/wnzceN>.

Rossa et al., "A Data-Driven Soft Sensor for Needle Deflection in Heterogeneous Tissue using Just-in-Time Modelling", Medical and Biological Eng. and Computing, 2016/2017, 55(8): 1401-1414.

Rossa et al., "Issues in Closed-Loop Needle Steering", Control Engineering Practice, 2017, 62: 55-69.

Khansari-Zadeh et al., "Learning Potential Functions from Human Demonstrations with Encapsulated Dynamic and Compliant Behaviors", Autonomous Robots, 2015, 41(1): 45-69.

Rossa et al., "Design Considerations for Magnetorheological Brakes", IEEE/ASME Transactions on Mechatronics, 2014, 19(5): 1669-1680.

(56) References Cited

OTHER PUBLICATIONS

Rossa et al., "Development of a multilayered wide-raged torque magnetorheological brake", Smart Material and Structures, 2014, 23(2): 025028 (10 pages).

* cited by examiner

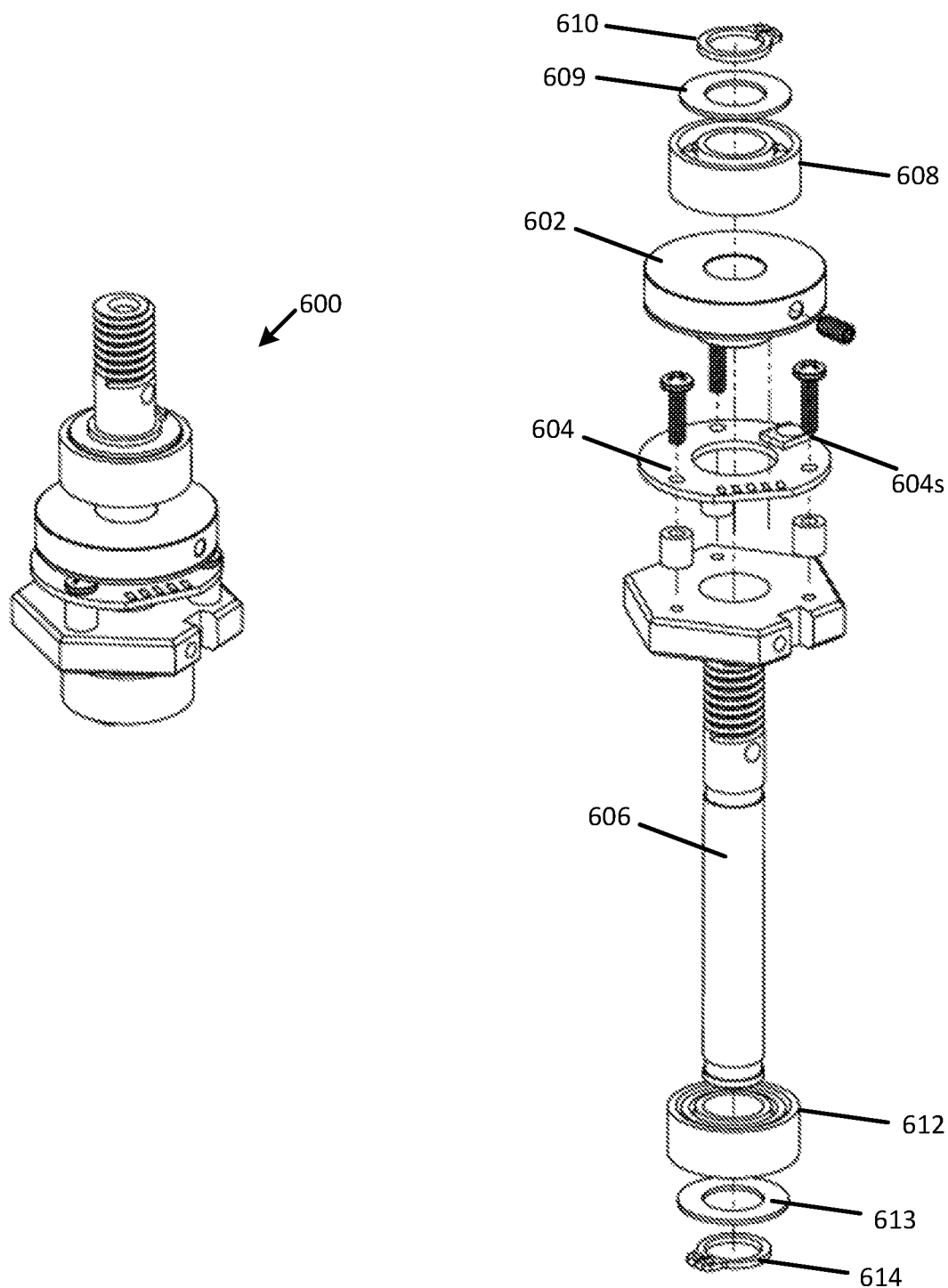
FIG. 6A  FIG. 6B

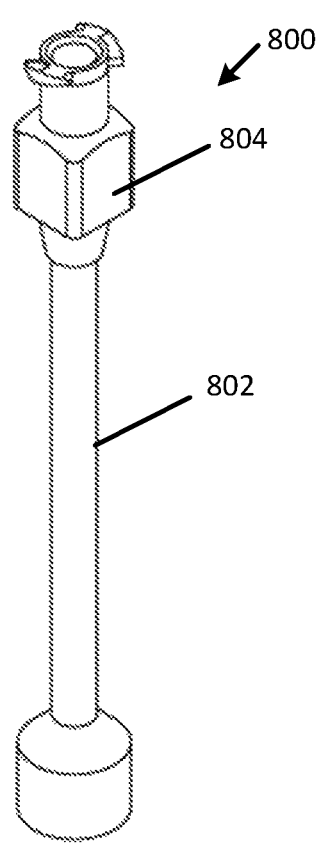
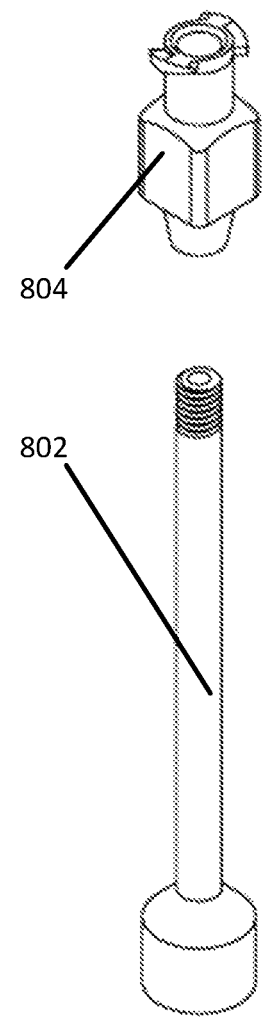
FIG. 8A
FIG. 8B

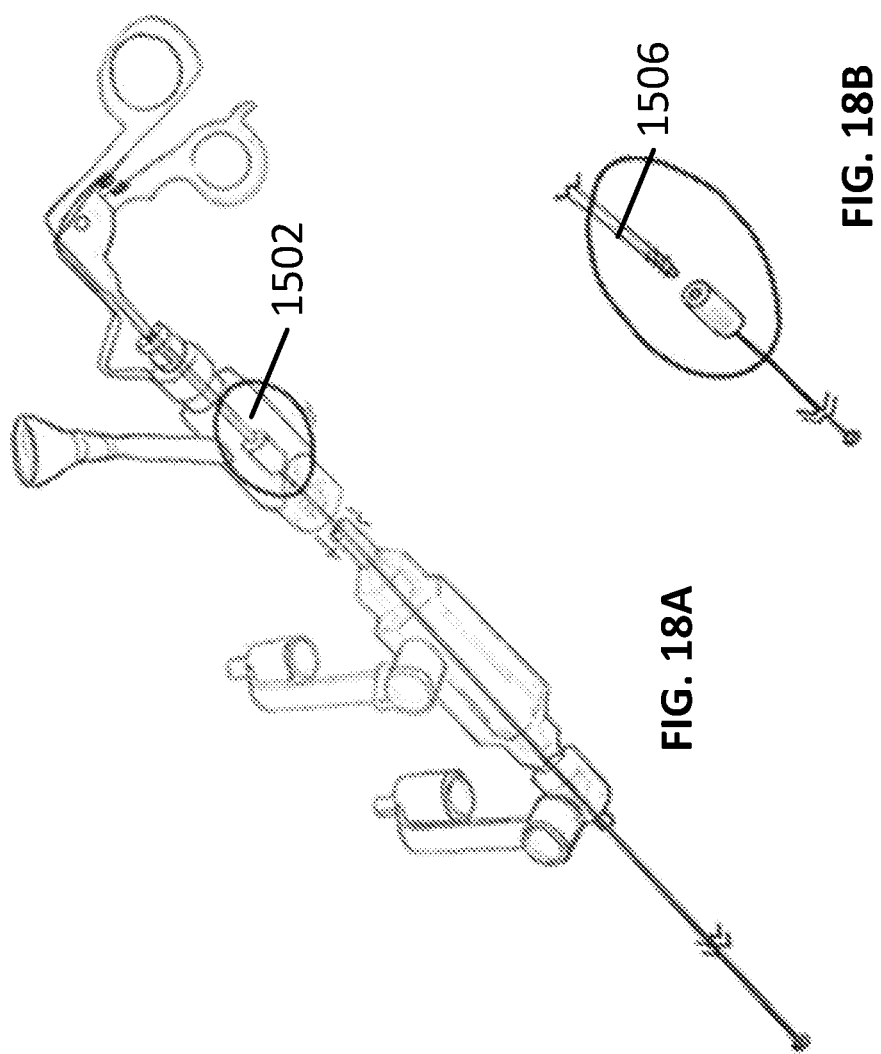

VIRTUAL REALITY SURGICAL SYSTEM INCLUDING A SURGICAL TOOL ASSEMBLY WITH HAPTIC FEEDBACK

CROSS-REFERENCE

This application claims the benefit of United States Provisional Patent Application No. 62/673,652, filed May 18, 2018, and the entire contents of U.S. Provisional Patent Application No. 62/673,652 is hereby incorporated by reference.

FIELD

This disclosure relates generally to apparatus, systems and methods for providing a surgical simulator, and more specifically to apparatus, systems and methods for providing a virtual reality surgical system including a needle and wire instrument.

BACKGROUND

Haptic-control robotics have been used for several years for simulating medical procedures and training surgeons. Haptic-control robotics can provide a surgeon with force feedback at a surgical instrument that emulates touch sensations, forced movement, any resistances to movement, or information that emulates the touch sensations of an actual surgery to create a realistic training scenario.

Virtual reality (VR) devices are also starting to emerge as surgical simulation devices for training surgeons. Virtual reality-based surgery simulation provides the surgeon with a 3D scene of the modelled organs on a computer screen or other display and can be combined with haptic feedback from haptic control robotics at the instrument handle of the surgical instrument.

To simulate minimally invasive procedures, these VR devices typically combine simulated images from medical equipment such as a laparoscopic camera with force feedback on the surgical instrument.

One difficulty with current simulators is that they typically do not provide a trainee with a realistic experience of being in an operating room. Furthermore, current simulation systems cannot provide haptic feedback from more than one surgical instrument as the interaction of forces between multiple surgical instruments—particularly when one instrument is used inside or alongside the other instrument—tends not to lend itself to a closed-form solution.

Accordingly, there is a need for new methods, systems and apparatuses for providing a VR surgical system with haptic feedback.

SUMMARY

In accordance with a broad aspect, there is provided an instrument for simulating surgical procedures in a virtual environment with haptic feedback. The instrument includes a tool assembly having an outer wall defining a cavity of the tool assembly; first and second brackets each having first shafts that are rotatably coupled at first and second end regions of the tool assembly and second shafts that are rotatably coupled to first and second robotic arms, allowing a user to move the instrument; a surgical tool assembly coupled to an end portion of the tool assembly and having an elongated member that extends within the tool assembly; an elongated member position sensor assembly housed within the cavity and configured to provide position information of a position of the elongated member of the instrument to a computing unit; and an elongated member force feedback assembly housed within the cavity and coupled to the elongated member, the elongated member force feedback assembly being configured to receive a control signal from the computing unit causing the elongated member force feedback assembly to apply a frictional force on the elongated member to provide haptic feedback to the user of the instrument when the computing unit detects a collision between at least one aspect of a patient anatomy and at least one of the tool assembly and the elongated member in the virtual environment.

In at least one embodiment, the instrument includes a tool rotation sensor assembly located at the tool assembly and coupled with the surgical tool assembly and configured to provide orientation information of an orientation of the surgical tool assembly to the computing unit.

In at least one embodiment, the tool rotation sensor assembly includes a code wheel having lines arranged thereon and a PCB configured to measure rotations of the code wheel based on the lines and to transmit the measurements the orientation of the surgical tool assembly.

In at least one embodiment, the elongated member position sensor assembly comprises an optical sensor to detect lateral and axial movement of the elongated member.

In at least one embodiment, the elongated member force feedback assembly includes moveable elements that move in response to the control signal to apply friction on the elongated member to provide the haptic feedback.

In at least one embodiment, the moveable elements comprise eccentric presses.

In at least one embodiment, the two eccentric presses press on opposed sides of the elongated member to provide the frictional haptic feedback.

In at least one embodiment, the elongated member force feedback assembly includes a motor coupled to the moveable elements and configured to direct the two moveable elements to apply the friction on the elongated member to provide the haptic feedback.

In at least one embodiment, the instrument includes a Gimbal assembly located at a bottom end portion of the tool assembly and coupled to the first shaft of the second bracket, the Gimbal assembly allowing for the tool assembly to be rotated about a longitudinal axis of the tool assembly.

In at least one embodiment, each of the first and second brackets include at least one rotary limiter along at least one of the first and second shafts, the first and second shafts each being coupled to the tool assembly and one of the robotic arms.

In at least one embodiment, the surgical tool assembly comprises a needle assembly and a wire assembly that is separate from the needle assembly longitudinally extends through the needle assembly and the tool assembly, is longitudinally moveable with respect to the needle member and the tool assembly, and comprises a wire that is the elongated member.

In at least one embodiment, the needle assembly is coupled to the tool rotation sensor assembly at an upper end portion of the tool assembly.

In at least one embodiment, the surgical tool assembly comprises a nephroscope having a nephroscope handle and a nephroscope grasper that is separate from the nephroscope handle and has a rod that longitudinally extends through the nephroscope handle and the tool assembly, is longitudinally moveable with respect to the nephroscope handle and the tool assembly, and acts as the elongated member.

In at least one embodiment, the nephroscope handle is coupled to the tool rotation sensor assembly at an upper end portion of the tool assembly.

In accordance with another broad aspect, a system for simulating surgical procedures in a virtual environment with haptic feedback is described. The system includes a Virtual Reality (VR) headset that is worn by a user; an instrument having a tool assembly, a surgical tool assembly coupled to and extending from an end of the tool assembly and an elongated member that is moveable through the tool assembly and the surgical tool assembly, the instrument being configured to: provide orientation information of an orientation of the surgical tool assembly; provide positional information of a position of the elongated member; and provide frictional force haptic feedback to the user in response to the position of the elongated member. The system also includes a sensor system configured to detect a position of at least a portion of the surgical tool assembly and provide position information of the position of the portion of the surgical tool assembly; at least one robotic arm coupled to the tool assembly, the robotic arm configured to provide applied force haptic feedback to the user in response to the position of the surgical tool assembly; and a computing unit in communication with the instrument, the sensor system and the at least one robotic arm, the computing unit being configured to: generate the virtual environment and output an image of the virtual environment to the VR headset display, the virtual environment including a model of a patient anatomy and a model of the surgical tool assembly; receive the orientation and position information of the surgical tool assembly and the elongated member and determine a surgical tool assembly location and orientation an elongated member location and orientation in the virtual environment; perform a physical simulation of the interaction between at least one of the surgical tool assembly and the elongated member and at least one aspect of patient anatomy; and transmit a first control signal to cause the instrument to provide the frictional force haptic feedback to the elongated member based on the physical simulation of the interaction; and transmit a second control signal to cause the at least one robotic arm to provide the applied force haptic feedback to the surgical tool assembly.

In at least one embodiment of the system, the computing unit is further configured to: generate an image of a C-arm in the virtual environment that is used to obtain virtual X-ray images showing the virtual interaction of the instrument with the patient anatomy; provide the user with the virtual X-ray images through voice commands or inputs provided to VR hardware by the user; and display the virtual X-ray images in the virtual environment on a virtual X-ray monitor.

In at least one embodiment of the system, the computing unit is further configured to: generate an image of an ultrasound device in the virtual environment that is used to obtain virtual ultrasound images showing the virtual interaction of the instrument with the patient anatomy; provide the user with the virtual ultrasound images through voice commands or inputs provided to VR hardware by the user; and display the virtual ultrasound images in the virtual environment on a virtual ultrasound monitor.

In at least one embodiment of the system, the computing unit is further configured to: generate an image of an endoscope device in the virtual environment that is used to obtain virtual endoscope images showing the virtual interaction of the instrument with the patient anatomy; provide the user with the virtual endoscope images through voice commands or inputs provided to VR hardware by the user; and display the virtual endoscope images in the virtual environment on a virtual endoscope monitor.

In at least one embodiment of the system, the system also includes a display that is communicatively coupled with the computing unit for displaying a given virtual image or a portion of the virtual environment.

In at least one embodiment of the system, the instrument, the at least one robotic arm and the display are mounted on a cart.

In accordance with another broad aspect, a method for simulating a medical procedure on a patient anatomy in a virtual reality environment and providing haptic feedback to a user who interacts with a physical instrument, the method being executed on at least one computing unit, is described herein. The method includes: executing, by a Virtual Reality (VR) simulator, a simulation of the medical procedure; receiving instrument location information corresponding to a location of at least a portion of the physical instrument; determining, by a surgical physics simulator, interaction between a virtual representation of the physical instrument and the patient anatomy; generating haptic control signals based on the determined interaction; rendering, by the VR simulator, a virtual reality operating room scene that corresponds to the medical procedure and indicates the interaction between the virtual representation of the physical instrument and the patient anatomy; displaying, by at least one of a virtual reality headset and a physical display, at least a portion of the rendered virtual reality operating room scene to the user; and providing haptic feedback to the physical instrument using the haptic control signals.

In at least one embodiment of the method, the method further includes allowing virtual X-ray images to be taken showing the interaction between the instrument and the patient anatomy in the virtual environment and displaying the X-ray image to the user via the virtual reality headset and/or the physical display.

In at least one embodiment of the method, the at least a portion of the rendered virtual reality operating room scene comprises a myopic view of the simulated surgery showing a close up view of an area of the patient anatomy where the simulated surgery is occurring.

In accordance with another broad aspect, a system for simulating surgical procedures on a patient anatomy in a virtual environment with haptic feedback is provided. The system comprises a Virtual Reality (VR) headset that is wearable by a user; a display; an instrument having a tool assembly, a surgical tool assembly coupled to and extending from an end of the tool assembly and an elongated member that is moveable through the tool assembly and the surgical tool assembly, the instrument being moveable by the user and being configured to provide orientation and position information of the surgical tool assembly and the elongated member and provide haptic feedback to the user in response to a haptics control signal; at least one robotic arm coupled to the tool assembly and configured to provide haptic feedback to the user; and a computing unit in communication with the instrument, the sensor system, the at least one robotic arm and the display. The computing unit is configured to receive the orientation and position information of the surgical tool assembly and elongated member; generate a virtual representation of the surgical tool assembly and the elongated member in the virtual environment based on the orientation and position information; determine an interaction between at least two of the virtual representation of the surgical tool assembly, the elongated member and the patient anatomy; generate the haptics control signal based on the interaction; and display an image of at least a portion of the surgical tool assembly, the elongated member, and the patient anatomy in the virtual environment on at least one of the VR headset and the display.

These and other features and advantages of the present application will become apparent from the following detailed description taken together with the accompanying drawings. However, it should be understood that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIG. 6A shows a front perspective view of a needle sensor assembly of the needle and wire instrument of FIG. 1, according to one example embodiment.

FIG. 6B shows an exploded front perspective view of the needle sensor assembly of FIG. 6A.

FIG. 8A shows a front perspective view of a needle assembly of the needle and wire instrument of FIG. 1, according to one embodiment.

FIG. 8B shows an exploded front perspective view of the needle assembly of FIG. 8A.

FIGS. 17A-18A show perspective and side views of an example embodiment of a nephroscope coupling to the instrument assembly of FIG. 4.

FIG. 18B shows a partial view of a grasper of the nephroscope of FIGS. 17A-18A.

Figure 1:
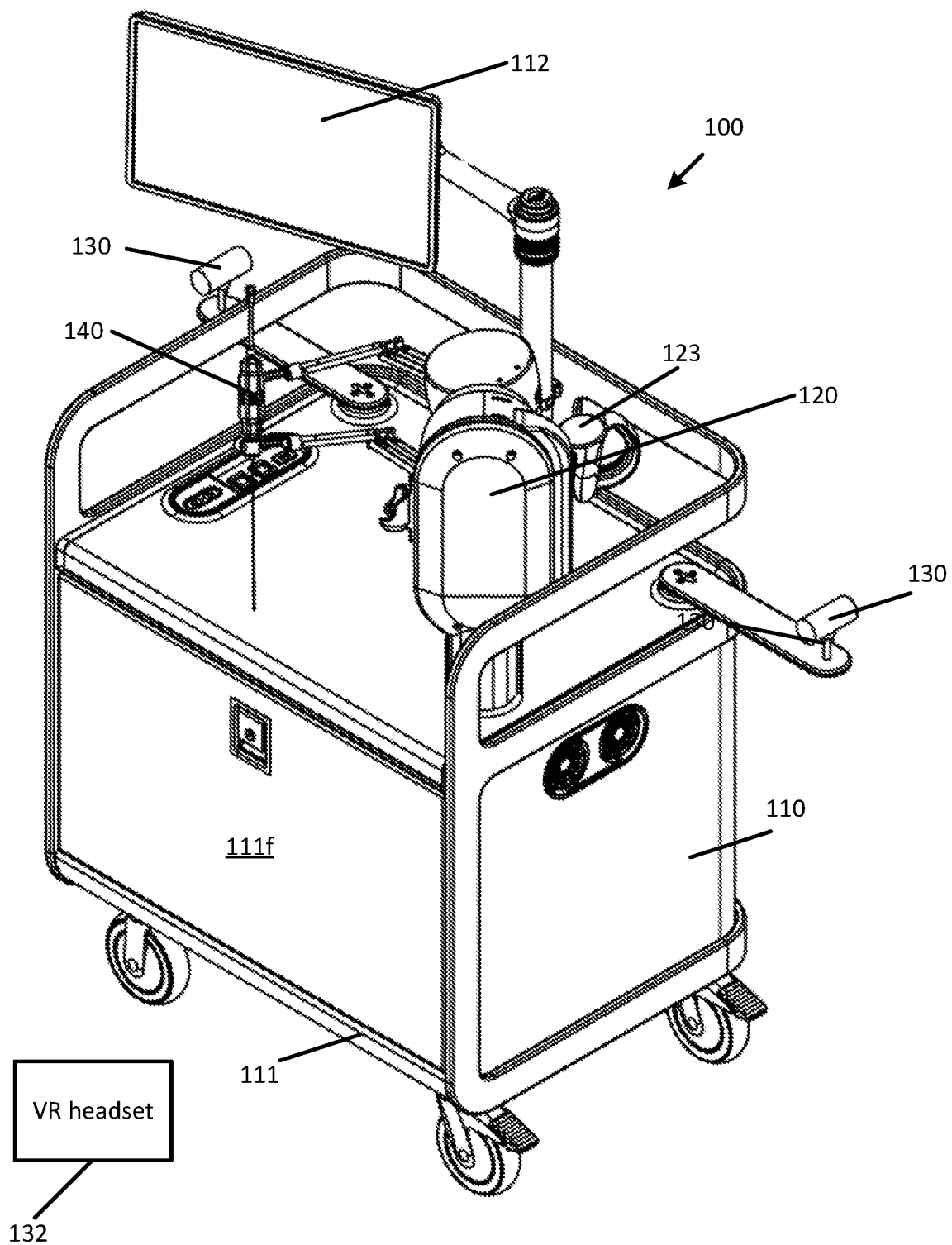
FIG. 1 shows a perspective view of an example embodiment of a virtual reality surgical system including a needle and wire instrument.

The skilled person in the art will understand that the drawings, further described below, are for illustration purposes only. The drawings are not intended to limit the scope of the applicant's teachings in any way. Also, it will be appreciated that for simplicity and clarity of illustration, elements shown in the figures have not necessarily been drawn to scale. For example, the dimensions of some of the elements may be exaggerated relative to other elements for clarity. Further aspects and features of the example embodiments described herein will appear from the following description taken together with the accompanying drawings.

DESCRIPTION OF EXAMPLE EMBODIMENTS

Various apparatuses, methods and compositions are described below to provide an example of at least one embodiment of the claimed subject matter. No embodiment described below limits any claimed subject matter and any claimed subject matter may cover apparatuses and methods that differ from those described below. The claimed subject matter are not limited to apparatuses, methods and compositions having all of the features of any one apparatus, method or composition described below or to features common to multiple or all of the apparatuses, methods or compositions described below. Subject matter that may be claimed may reside in any combination or sub-combination of the elements or process steps disclosed in any part of this document including its claims and figures. Accordingly, it will be appreciated by a person skilled in the art that an apparatus, system or method disclosed in accordance with the teachings herein may embody any one or more of the features contained herein and that the features may be used in any particular combination or sub-combination that is physically feasible and realizable for its intended purpose.

Furthermore, it is possible that an apparatus, method or composition described below is not an embodiment of any claimed subject matter. Any subject matter that is disclosed in an apparatus, method or composition described herein that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

It will also be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

It should be noted that terms of degree such as "substantially", "about" and "approximately" as used herein mean a reasonable amount of deviation of the modified term such that the result is not significantly changed. These terms of degree should be construed as including a deviation of the modified term, such as 1%, 2%, 5%, or 10%, for example, if this deviation would not negate the meaning of the term it modifies.

Furthermore, the recitation of any numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation up to a certain amount of the number to which reference is being made, such as 1%, 2%, 5%, or 10%, for example, if the end result is not significantly changed.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

In spite of the technologies that have been developed, there remains a need in the field for improvements in the development of virtual reality surgical simulators with haptic feedback.

Generally, a virtual reality surgical system with haptic feedback is described herein. The system can be used to simulate a wide variety of instruments and surgeries including, but not limited to, the needle wire instrument described herein, for example. The needle and wire instrument described below can be used to simulate a wide variety of surgeries or other medical procedures. For example, the needle wire instrument may be used to simulate a laparoscopic nephrectomy. Further, portions of the needle wire instrument can be used individually to simulate surgeries or other medical procedures. For example, the wire assembly can be used alone (with the needle portion being held in place and not impacting the simulation) to simulate catheter insertion into a vein as part of heart, brain tumor-related or other types of surgeries. In another example, the needle instrument can be used alone for simulating IV insertions or spinal needle insertions such as a lumbar puncture in difficult cases or selective nerve blocking.

Turning to the Figures, FIG. 1 shows a perspective view of a Virtual Reality (VR) surgical system 100 including a needle and wire instrument 140. The VR surgical system 100 includes a medical cart 111 with a base 110, a display 112 mounted to the base 110, a haptic arm assembly 120 mounted to the base 110, one or more VR sensors 130 coupled to the base 110, the haptics arm assembly 120, or any other part of the VR surgical system 100. The needle and wire instrument 140, which may also be referred to as the tool, is coupled to the haptic arm assembly 120.

The VR surgical system 100 also comprises a VR headset 132 that is worn by the user while they are performing the surgical simulation to view a Virtual Reality Operating Room (VR OR). The VR headset 132 may be an Oculus headset or an HTC Vive™ headset, for example. The VR OR includes a virtual view of a portion of the patient where the surgery is being performed, a virtual view of the tool that is used to perform the surgery, a virtual view of a C-arm, and a virtual X-Ray monitor. In the physical world, the C-arm is an imaging device that is used in an OR to obtain X-ray images of a surgical site. In the VR OR, the virtual C-arm is used to obtain virtual X-ray images of the surgical site that are shown on the virtual X-ray monitor. This can be done by taking the current position and rotation (i.e. to get current coordinates) of the virtual C-arm within the simulation and composing a simulated x-ray image determined from a physics simulation via the surgical physics simulator 1302 using the current coordinates (e.g.: by ray-tracing through the models with each model having a specific 'density'). The image can then be displayed within the VR OR on any number of virtual monitors for the surgeon to take note of. The C-arm and/or other purely virtual tools may be included in the VR OR based on the type of surgery being simulated and the need of including such tools within it. In some embodiments; the VR surgical system 100 may provide an augmented view to the user. In these embodiments, the VR headset 132 may be configured to display the augmented view which comprises an overlay of a virtual view over a real-world view, where the virtual view has virtual objects that may be generated in a similar manner as described for the VR views discussed herein.

In some cases or select surgery types it may not be necessary to use the virtual C-arm or the x-ray views, as other types of imaging techniques may be simulated and used. Alternatively, in at least one embodiment, the virtual C-arm and the x-ray views can be used with other types of imaging techniques. Examples of other imaging techniques that may be used include standard imaging cameras (e.g.: at the end of a laparoscopy or other endoscopic medical instrument) or ultrasound devices which can provide endoscopy and ultrasound views, respectively. Such instruments may be purely virtual tools as in the case of the C-arm. Accordingly, in some embodiments, there may also be at least one of: (a) a virtual endoscope device and a corresponding virtual endoscope monitor and (b) a virtual ultrasound device and a corresponding virtual ultrasound monitor. In these cases, the current position and rotation of the virtual endoscope device and/or virtual ultrasound device within the simulation can be obtained (La to get current coordinates) and a simulated endoscope image and/or simulated ultrasound image can be generated from a physics simulation that is provided by the surgical physics simulator 1302 using the current coordinates (e.g.: by ray-tracing through the models with each model having a specific 'density').

The base 110 can be any appropriate base for supporting the display 112, the haptic arm assembly 120 and the VR sensors 130. The base 110 may be a stationary base or may be portable. For instance, in the example embodiment shown in FIG. 1, the base 110 is a portable medical cart and the display 112, the haptic arm assembly 120 and the VR sensors 130 are mounted to a top surface of the medical cart. The base 110 may be configured to house other electronic equipment associated with the haptic arm assembly 120.

The display 112 is communicatively coupled to the haptic arm assembly 120 and configured to show images relating to the surgery being performed by a user, such as a surgeon, of the VR surgical system 100. For example, the display 112 may show the surgeon X-ray images that indicate the position of a virtual representation of a portion of the needle and wire instrument 140 within a virtual patient during a virtual surgery. The display 112 may also be used prior to the surgery to display various options provided by the VR surgical system 100 to the user including, but not limited to, the type of surgical simulation to perform, patient options (such as but not limited to gender, age, number of stones, size of kidney stones, and kidney stone complexity), user selection, the live-view that the user is currently seeing on the VR headset, an overhead view of the surgery room to be shown on the display 112, and to play back a previously completed surgery on the display 112, for example.

The haptic arm assembly 120 includes at least one robotic arm for carrying the needle wire instrument 140. In the embodiments shown in the figures, the haptic arm assembly 120 includes two robotic arms 122, 124 for carrying the needle and wire instrument 140. In the embodiment shown in the figures, the robotic arms 122, 124 including robotic haptics boards 1306a and 1306b were purchased from Entact Robotics Inc., Toronto Ontario. The haptic arm assembly 120 provides force feedback (e.g. haptic or tactile feedback) to the user as the user manipulates the needle and wire instrument 140 during the surgery. The haptic arm assembly 120 is communicatively coupled to a sensor system 130 configured to detect a position of VR tracker 123 (see FIGS. 1 and 10-12). The sensor system 130 provides the position of the VR tracker 123 to the haptic arm assembly 120, which also receives a position and rotation of the needle and wire instrument 141 relative to a home position to determine the exact position of the needle wire instrument 140 within the virtual environment. The haptic arm assembly 120 includes one or more computing units (not shown but provided within the haptic arm assembly 120) that are communicatively coupled with the needle and wire instrument 140 and the robotic arms 122,124. The haptic arm assembly 120 is further described below with reference to FIGS. 11 to 13.

Figures 2A, 2B:
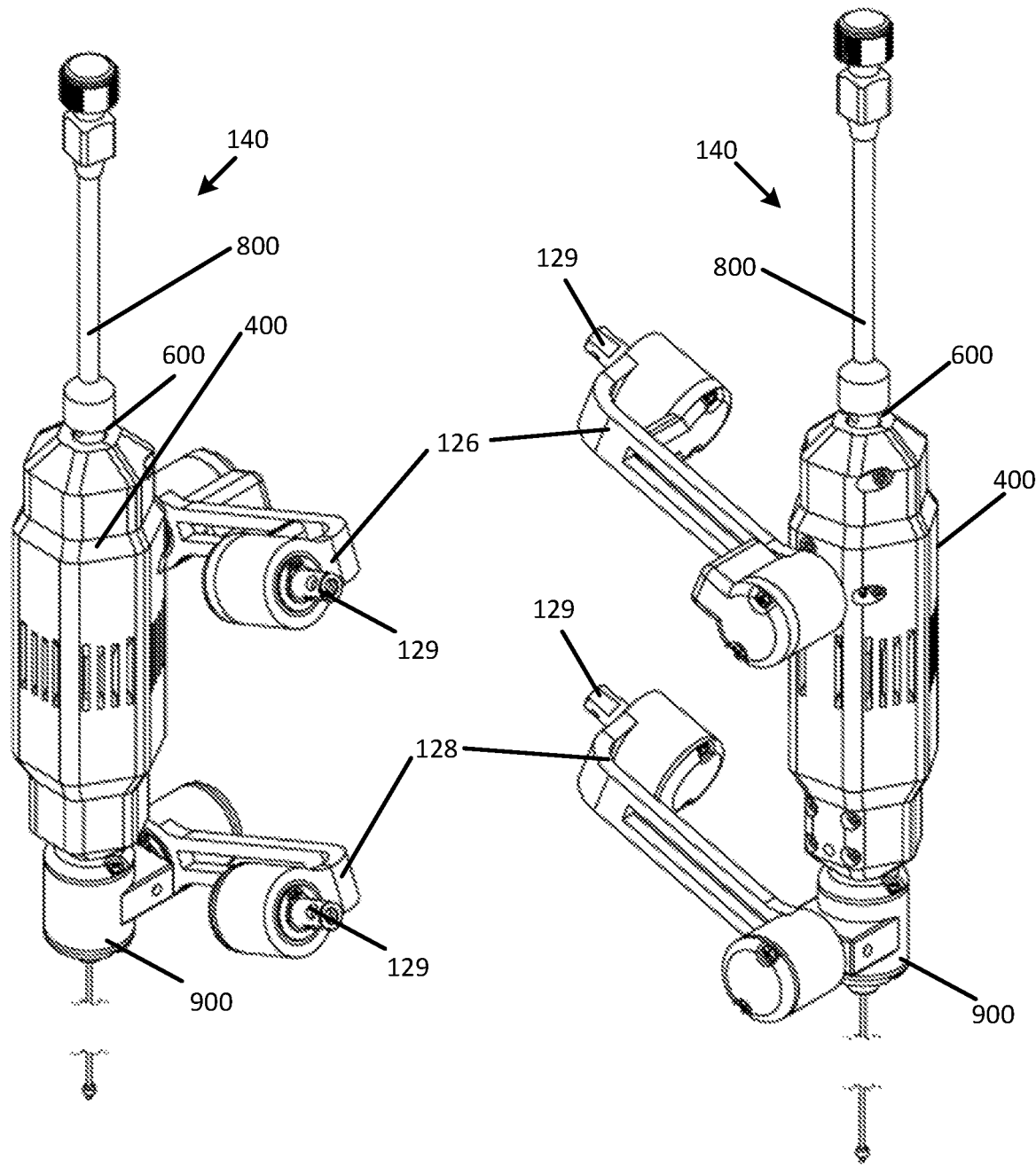
FIG. 2A shows a front perspective view of an example embodiment of the needle and wire instrument of the system of FIG. 1.
FIG. 2B shows a rear perspective view of an example embodiment of the needle and wire instrument of the system of FIG. 1.
Figure 3:
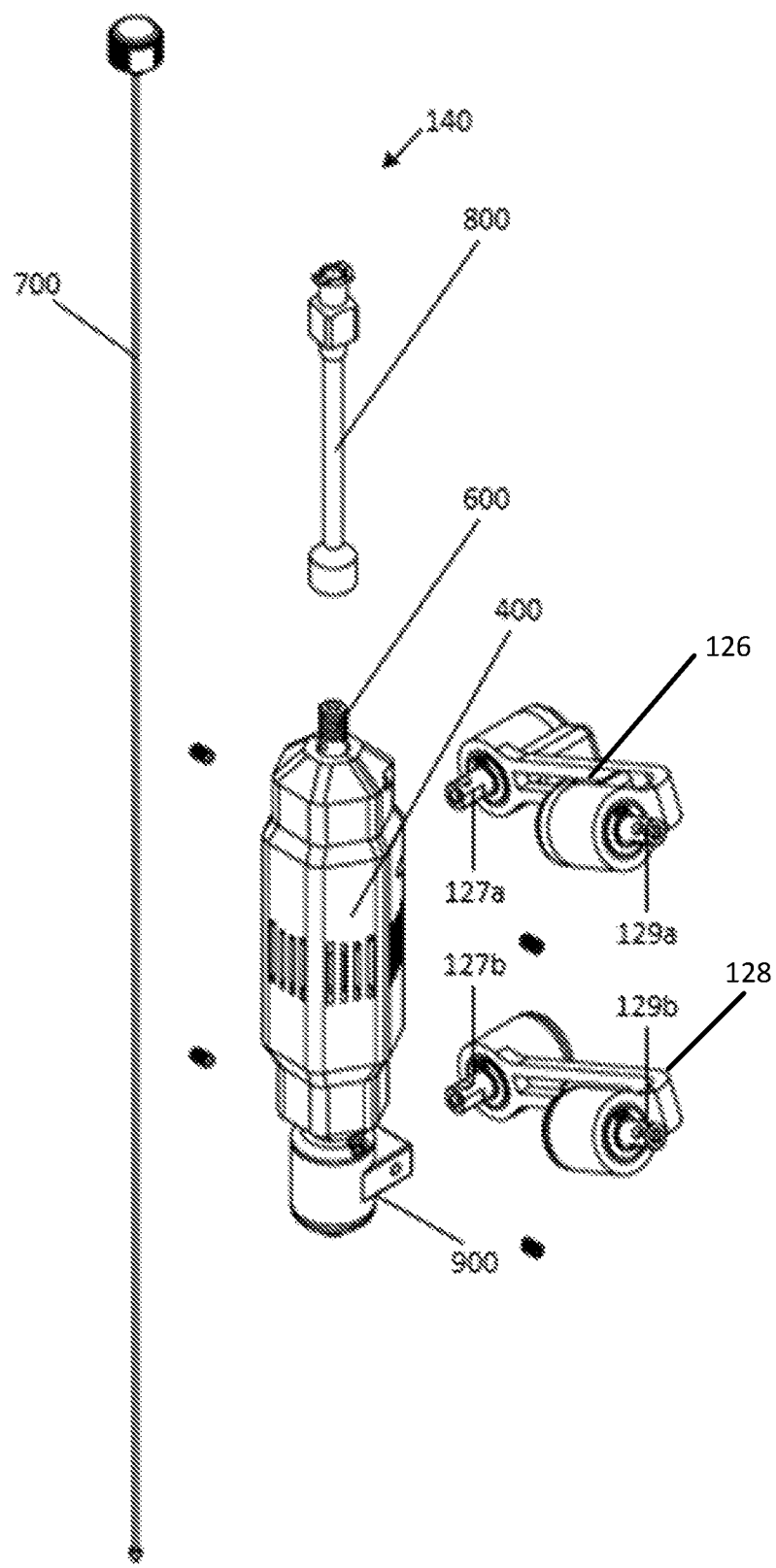
FIG. 3 shows an exploded front perspective view of the needle and wire instrument of FIG. 2 showing the instrument assembly, the needle assembly, the wire assembly and two brackets, according to one example embodiment.

Referring now to FIGS. 2A, 2B and 3, illustrated therein are front and rear perspective views as well as an exploded view, respectively, of an example embodiment of the needle and wire instrument 140, in accordance with the teachings herein. The needle and wire instrument 140 includes a tool assembly 400, a needle rotation sensor assembly 600 (see FIGS. 6A and 6B), a wire assembly 700 (see FIGS. 7A and 7B), a needle assembly 800 (see FIGS. 8A and 8B), a bottom Gimbal assembly 900 (see FIGS. 9A and 9B) and bracket assemblies 1000 (see FIG. 10). The needle and wire instrument 140 is carried by the haptic arm assembly 120 via robotic arms 122, 124 that are coupled to the needle and wire instrument 140 via a first bracket 126 and a second bracket 128. Any electrical wiring for the sensors 130 and for providing haptic feedback for the tool may be connected to the haptics arm assembly 120 through a top bracket 126 and further through the top robotic arm 122. In other embodiments, the wiring can be provided in an alternate fashion.

The first bracket 126 and the second bracket 128 are shown in FIGS. 2A and 2B. Each of the first bracket 126 and the second bracket 128 has a first bracket shaft 127a and 127b (see FIG. 3B), respectively, for rotatably coupling a first portion of the brackets 126 and 128 to the needle and wire instrument 140. Each of the first bracket 126 and the second bracket 128 also have a second bracket shaft 129a and 129b, respectively, for rotatably coupling a second portion of the brackets 126 and 128 to one of the robotic arms 122, 124. More specifically, the first bracket shaft 127a of the first bracket 126 is rotatably coupled to the tool assembly 400 and the first bracket shaft 127b of the second bracket 128 is coupled to the bottom Gimbal assembly 900. In some embodiments, the first and second bracket shafts 127 and 129 may be 6 mm shafts. In the embodiments shown in the drawings, the first and second brackets 126, 128, respectively, are configured to provide for the first bracket shafts 127 and the second bracket shafts 129 to freely rotate about their axis while restricting lateral movement. Each of the first and second bracket shafts 127 and 129 may be bolted in place to restrict their lateral movement. Either or both of the brackets 126 and 128 may be used to house wiring that runs from the tool assembly 400 to the base 110 so as to communicatively couple the tool assembly 400 to one or more computing units (not shown) that are within the base 110. In the example embodiment shown in the drawings, the top bracket 126 may be used to house the wiring. Limiters, for example limiters 1007 in FIG. 10, may be placed within the brackets so as to limit rotary movement to set angles thus preventing gimbal lock, wire wear, or other detrimental conditions.

As previously described, the tool assembly 400 is attached to the robotic arms 122 and 124 via the first and second brackets 126 and 128, respectively. Whenever the tool assembly 400 is moved by robotic arms 122 and 124, the positions of two connection points including a first connection point between an end of the first bracket shaft 127a and a first portion of the tool assembly 400 and a second connection point between an end of the second bracket shaft 127b and a second portion of the tool assembly 400. For example, the ends of the shafts 127a and 127b that couple to the first and second portions of the tool assembly 400 may include a first connection point which is at an intersection point between an axis passing through the first bracket shaft 127a and the second bracket shaft 129a of the first bracket 126 and a second connection point that is at an intersection point between an axis passing though first bracket shaft 127b and second bracket shaft 129b of the second bracket 128. Each of the connection points is unique depending on the position of the tool assembly 400, so in any unique position of the tool assembly 400, the first connection point of the top robotic arm 122 is at (x1,y1,z1) and the second connection point for the bottom robotic arm 124 is at (x2,y2,z2) which together provide a combined vector having end points (x1,y1,z1) and (x2,y2,z2) which will be unique and represent the position and rotation of the tool assembly 400 in real-space. Together those two connection points represent the exact position and rotation of the tool assembly 400 in real-space, which a VR simulation engine can then use to calculate the position of the tool assembly in the virtual environment.

The use of two robotic arms 122 and 124 to hold the tool allows a full 5 degrees of freedom in terms of movement and feedback for the tool. However, there is a physical limitation imposed on the possible positions that the tool can inhabit due to the possibility of mechanical interaction between the two robotic arms 122 and 124 which touch for movement of the tool along certain directions and thus prevent any further movement along that direction. For example, the coupling of the robotic arms 122 and 124 to the tool may prevent the tool from being flipped upside down. This limitation does not exist in real life since the physical tool is not connected to anything, and this is therefore an artificial limitation imposed on the VR surgical system. In order for this not to adversely impact the surgical simulation, a 45 degree configuration of the robotic arms 122 and 124 with respect to the front panel 111f of the medical cart 111 may be selected to provide for the tool to be held in the vast majority of typical tool positions during actual surgeries, while simultaneously keeping the robotic arms 122 and 124 away from the user's hands during both left handed and right handed operation. However, in other embodiments, the tool 400 may be attached to the robotic arms 122 and 124 with a different configuration than the 45 degree configuration of the robotic arms 122 and 124 with respect to the front panel 111f of the medical cart 111 described above to more accurately mimic real life surgery conditions. For example, 0, 45, or 90 degree configurations may all be viable for specific surgery types or for specific styles of surgery operations based on both the surgery being simulated and the methodology of the surgeons being targeted.

Figure 4:
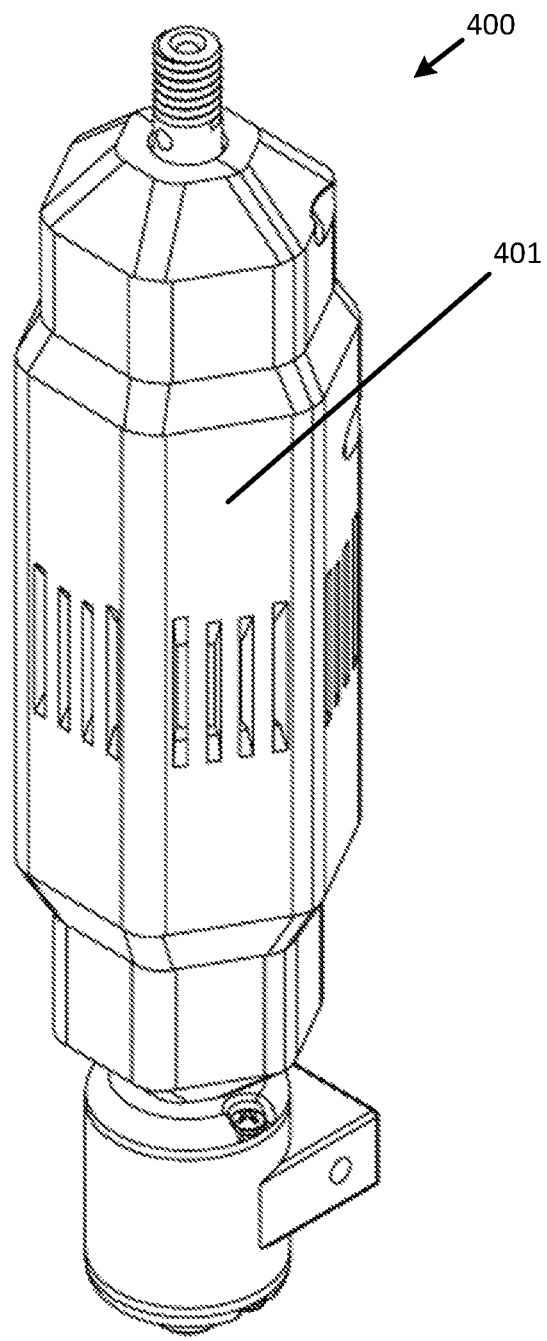
FIG. 4 shows a front perspective view of the instrument assembly of the needle and wire instrument of FIG. 1.
Figure 5:
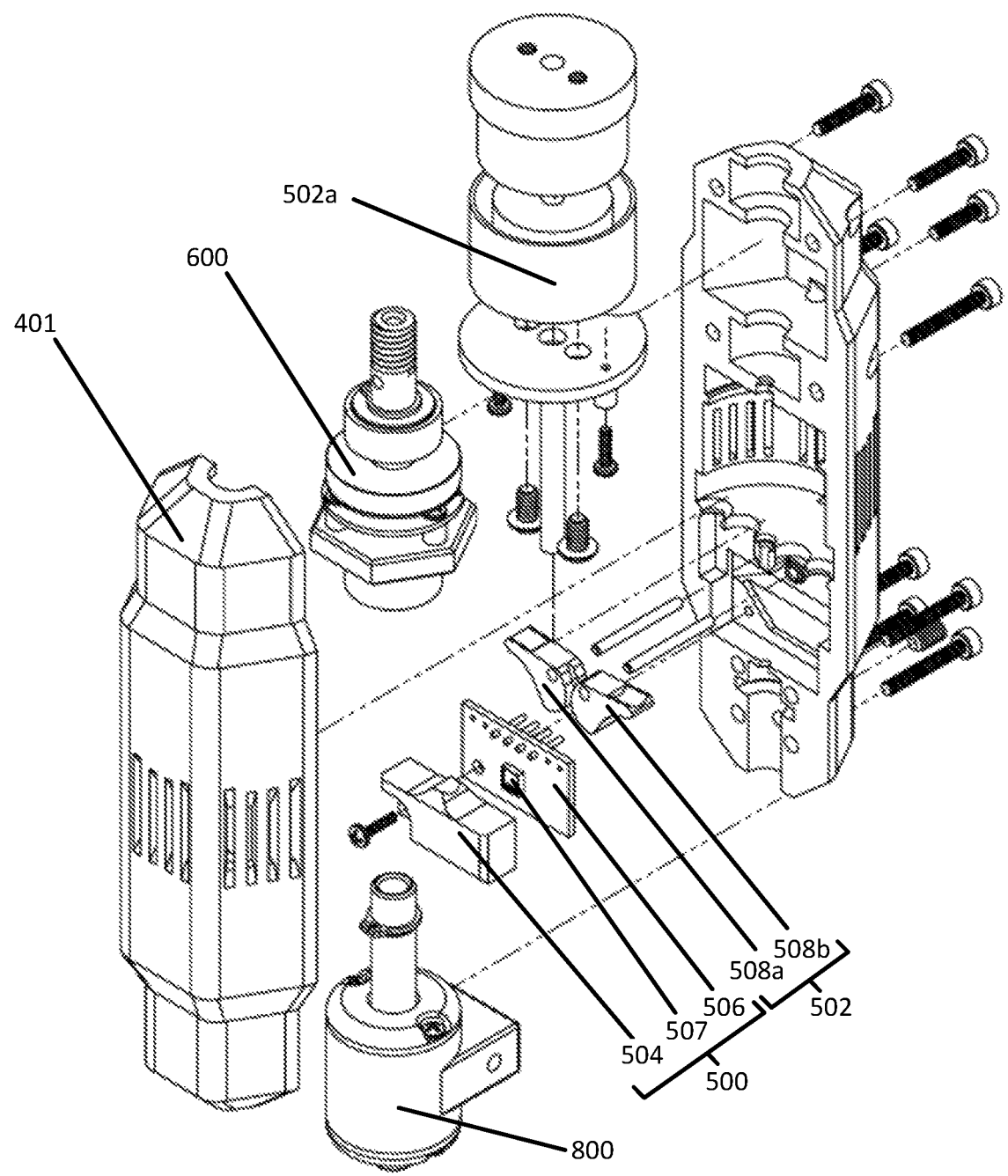
FIG. 5 shows an exploded front perspective view of the instrument assembly of the needle and wire instrument of FIG. 4.

Referring now to FIG. 4, illustrated therein is a perspective view of a tool assembly 400 of the needle and wire instrument 140, according to one embodiment. The tool assembly 400 has a housing 401 that defines a cavity therein for housing components of the tool assembly 400. The housing 401 may be made of any material having sufficient strength to withstand the forces applied by the robotic arms 122 and 124. For example, the housing 401 may be made using nylon plastic (e.g. using additive manufacturing) although any strong and lightweight material would work. The tool assembly 400 houses at least a portion of each of wire position sensor assembly 500, the wire force feedback assembly 502, the needle rotation sensor assembly 600, the wire assembly 700, the needle assembly 800 and the bottom Gimbal assembly 900. FIG. 5 shows an exploded perspective view of the embodiment of tool assembly 400 shown in FIG. 4, showing the internal components housed in housing 401. In some embodiments, the housing 401 may have an inner surface that define a cavity and is also shaped to conform to the components housed therein. In some embodiments, the housing 401 may be comprised of two housing portions that are couplable via coupling mechanisms (e.g. screws or bolts) for positioning and retaining the internal components of the tool assembly 200 inside of the housing 401.

Sensors indicating movement and/or position of at least a portion of the wire assembly 700 can be provided to the user of the tool assembly 400 by the wire position sensor assembly 500. The wire position sensor assembly 500 includes an optical sensor 507 on a circuit board 506 and a seclusion cover 504. Haptic feedback responsible for the user feel of wire insertion can be provided to the user of the tool assembly 400 by the wire force feedback assembly 502. The wire force feedback assembly includes a voice coil motor (VCM) 502a, and movable elements (e.g. eccentric presses) 508a and 508b.

The VCM 502a is configured to apply a force (e.g. by sliding downwardly) along its central axis. The operation of the VCM 502a is governed by a micro-controller (e.g. an Arduino). The applied force is applied equally to the two eccentric presses 508a, 508b. The eccentric presses 508a, 508b are positioned on opposed sides of the wire 704 (see FIG. 7B). The eccentric presses 508, 508b are configured to press on one of the two sides of the wire 704 to apply a friction force to the wire 704 to provide haptic feedback to the user as the user tries to slide the wire 704 through the tool assembly 400. Conversely, to reduce friction on the wire 704, the VCM 502a can retract (e.g. slide upwardly) and reduce the force that is applied to the eccentric presses 508a, 508b thereby moving them away from the wire 704.

The circuit board 506 has an optical sensor 507 that is positioned adjacent to the eccentric presses 508a, 508b such that the optical sensor 507 is below and laterally offset from the eccentric presses 508a, 508b so that the wire 704 passes first between the eccentric presses 508a, 508b and then through the seclusion cover 504 and in front of the optical sensor 507. This allows the optical sensor 507 to detect the wire 704 and determine the position of the wire 704. The position of the wire 704 can be calculated based on the position of the tool assembly 400 (the wire 704 is always concentric to the tool assembly 400) and the optical sensor 507 positioned inside of the tool assembly 400. For example, the optical sensor 507 can detect and report the axial movement of the wire 704 as the wire 704 passes in front of the optical sensor 507 and/or rotation of the wire 704 relative to the tool assembly 400. In this embodiment of the instrument 140, the optical sensor 507 operates using a laser emitter-receiver pairing that detects the texture of the wire 704 and calculates the most likely movement of the wire 704 (either laterally or axially) based on previously detected data. This allows the use of a wide variety of wires besides the wire 704 shown in this embodiment. The circuit board 506 provides the optical measurement from optical sensor 507 to the controller (e.g. Arduino) within the haptic arm assembly 120, which inputs the information to a surgical physics simulator 1302 via the an input/output (IO) interface 1305.

In at least some embodiments, the laser of the optical sensor 507 can be a very low powered laser (e.g. classified as a class 1 laser) and is aimed at the object (in this case the wire 704) and the reflections of the laser are detected by the optical sensor 507. The processor of the circuit board 506 then 'maps' out the texture (e.g. determines a bump map) of the wire 704 and compares it to a previous scan to determine the most likely displacement, which in this case corresponds to lateral and axial movement, and stores this displacement. When the processor of the circuit board 506 is polled (e.g. via I2C protocol) by the micro-controller 1308, it provides the cumulative displacement since the last poll resets the displacement to 0 and continues on. The micro-controller 1308 typically polls the optical sensor 507 much less frequently than the rate at which the optical sensor 507 reads the displacement (e.g. polling at ~100-1000 times a second compared to the sensor's rate of 10,000+ second). The accumulated displacement that is determined since the last poll is then added to the stored 'actual position' to calculate the new position, which is then sent to the surgical system control unit 1301.

Referring now to FIGS. 6A and 6B, illustrated therein are perspective and exploded perspective views of the needle rotation sensor assembly 600. The needle rotation sensor assembly 600 is configured to provide orientation information for an orientation of the needle assembly 800 to a computing unit within the haptic arm assembly 120.

The needle rotation sensor assembly 600 includes a code wheel 602 and a printed circuit board (PCB) 604 carrying a sensor 604s. The code wheel 602 is positioned above the PCB 604. The code wheel 602 has fine lines drawn on its lower surface which faces the PCB 604. The sensor 604s on the PCB 604 can detect the fine lines of the code wheel 602 as the code wheel 602 rotates. The number of lines that cross over (i.e. move by) the sensor 604s are counted and are converted to the angle that the code wheel 602 has rotated. The code wheel 602 is coupled to main shaft 606 and therefore the code wheel 602 rotates accordingly to the angle that the shaft (and thus the tool attached to it—in this case the needle 704) has rotated.

In some embodiments, it may not be possible to use the sensor 604s to determine an exact position of the shaft 606, but rather a relative angle that the code wheel 602 has moved (e.g. rotated) since the instrument 140 was first being used. In this embodiment, the software is not provided with the exact angle of the instrument 140 and initial homing may be used to calibrate this position. In some embodiments, code wheel 602 may be an absolute rotary encoder.

Figure 17A:
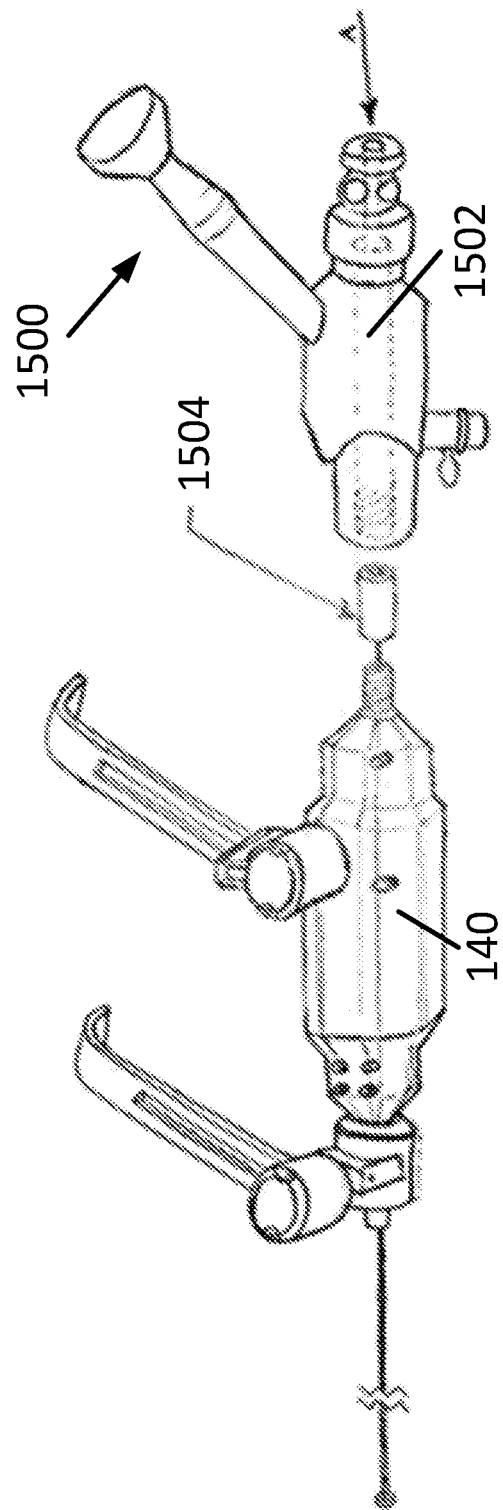
Figure 17B:
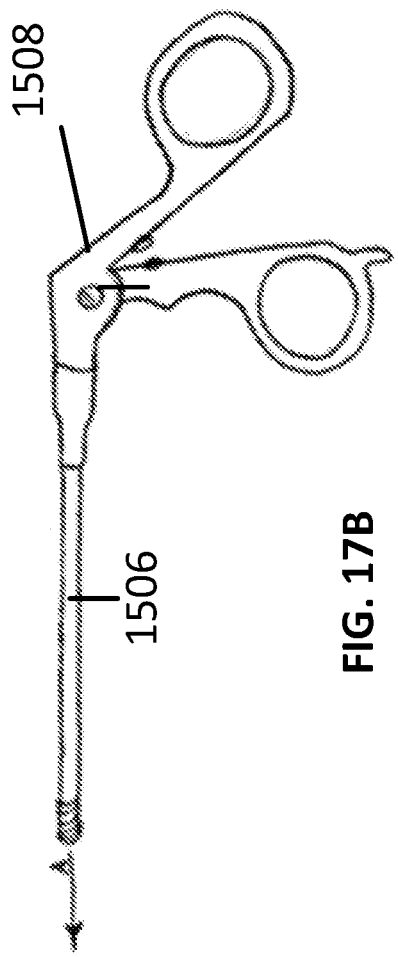

The needle rotation sensor assembly 600 may also include ball bearings 608 and 612 at opposed ends of main shaft 606 to reduce rotational friction and support radial and axial loads between the main shaft 606 and the tool assembly 400. In some embodiments, the ball bearings may be Igus ball bearings having a 6 mm inside diameter, 13 mm outside diameter and 5 mm thickness. In other embodiments, the ball bearings 608, 612 can have other diameters to accommodate main shaft 606 having a diameter in a range of about 4 mm to 6 mm, or at least 6 mm in this example embodiment (for other embodiments, these dimensions may change). Washers 609 and 613 as well as retaining rings 610 and 614 can be used to hold the bearings 608 and 612 in place and inhibit lateral movement of the main shaft 606. It should be noted that in alternative embodiments, the ball bearings 608 and 612 may be modified to allow for attaching to a wide array of tool-tips for providing surgical simulations using different types of tools (an example of another tool that can be used is provided in FIGS. 17A-17B).

As previously described, the needle rotation sensor assembly 600 is communicatively coupled to the computing unit (i.e. micro-controller 1308 shown in FIG. 15) and configured to provide information of the orientation of the needle assembly 800 to the computing unit.

Figures 7A, 7B:
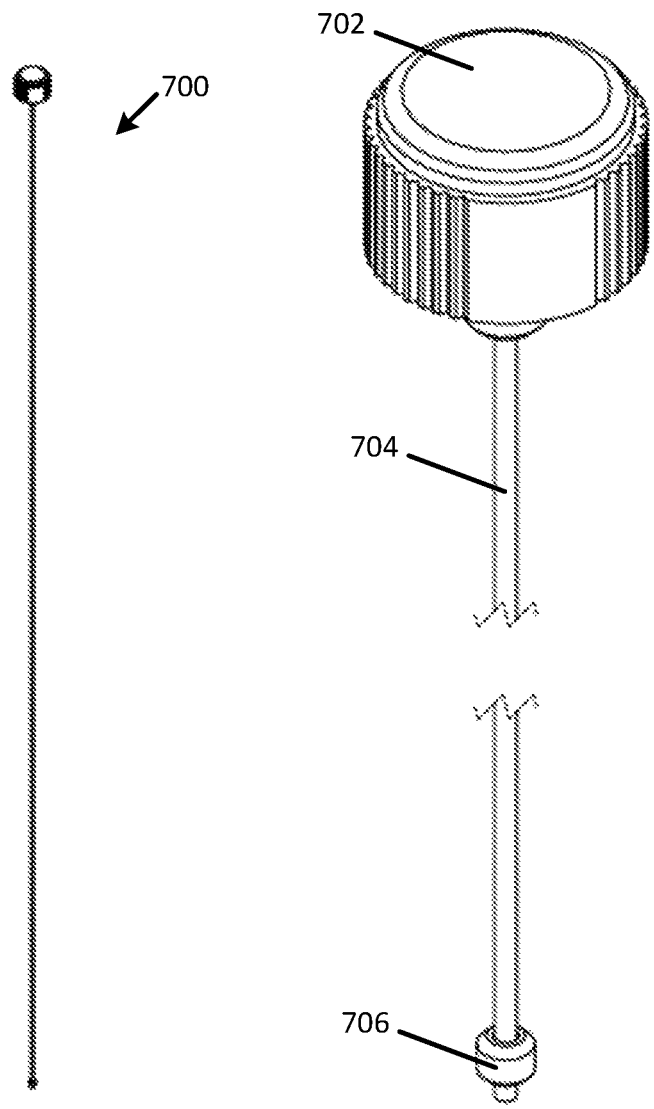
FIG. 7A shows a front perspective view of a wire assembly of the needle and wire instrument of FIG. 1, according to one example embodiment.
FIG. 7B shows a magnified view of certain portions of the wire assembly of FIG. 7A.

Referring now to FIGS. 7A and 7B, illustrated therein are perspective views of the wire assembly 700. The wire assembly 700 includes a head portion 702, a wire 704 and an end portion 706. The head portion 702 is coupled to one end of the wire 704 and provides a structure for the surgeon to manipulate the wire 704. In some embodiments, the user may use the wire assembly 700 to mimic a portion of a minimally invasive surgical instrument such as, but not limited to, a catheter or graspers, for example. In some embodiments the end portion 706 can be included to prevent the full removal of the wire 700 from the tool assembly 400, while for other types of tool tips it can be left out to provide for usage of different wires. Accordingly, the end portion 706 may be optional in certain embodiments.

Referring now to FIGS. 8A and 8B, illustrated therein are perspective views of the needle assembly 800. The needle assembly 800 includes a main shaft 802 and a top portion 804. The top portion 804 is rotationally coupled to the main shaft 802. Each of main shaft 802 and the top portion 804 have a channel extending therethrough for receiving the wire 704 of the wire assembly 700 therein. The top portion 804 may be used to allow the wire 700 assembly to 'screw' in and mimic the inner needle which gets pulled out of the main needle during surgery prior to the insertion of the wire. In some embodiments, the user can use an alternate tool-tip (see for example FIG. 18A) to mimic a portion of another minimally invasive surgical instrument such as, but not limited to, a nephroscope, for example.

Figures 9A, 9B:
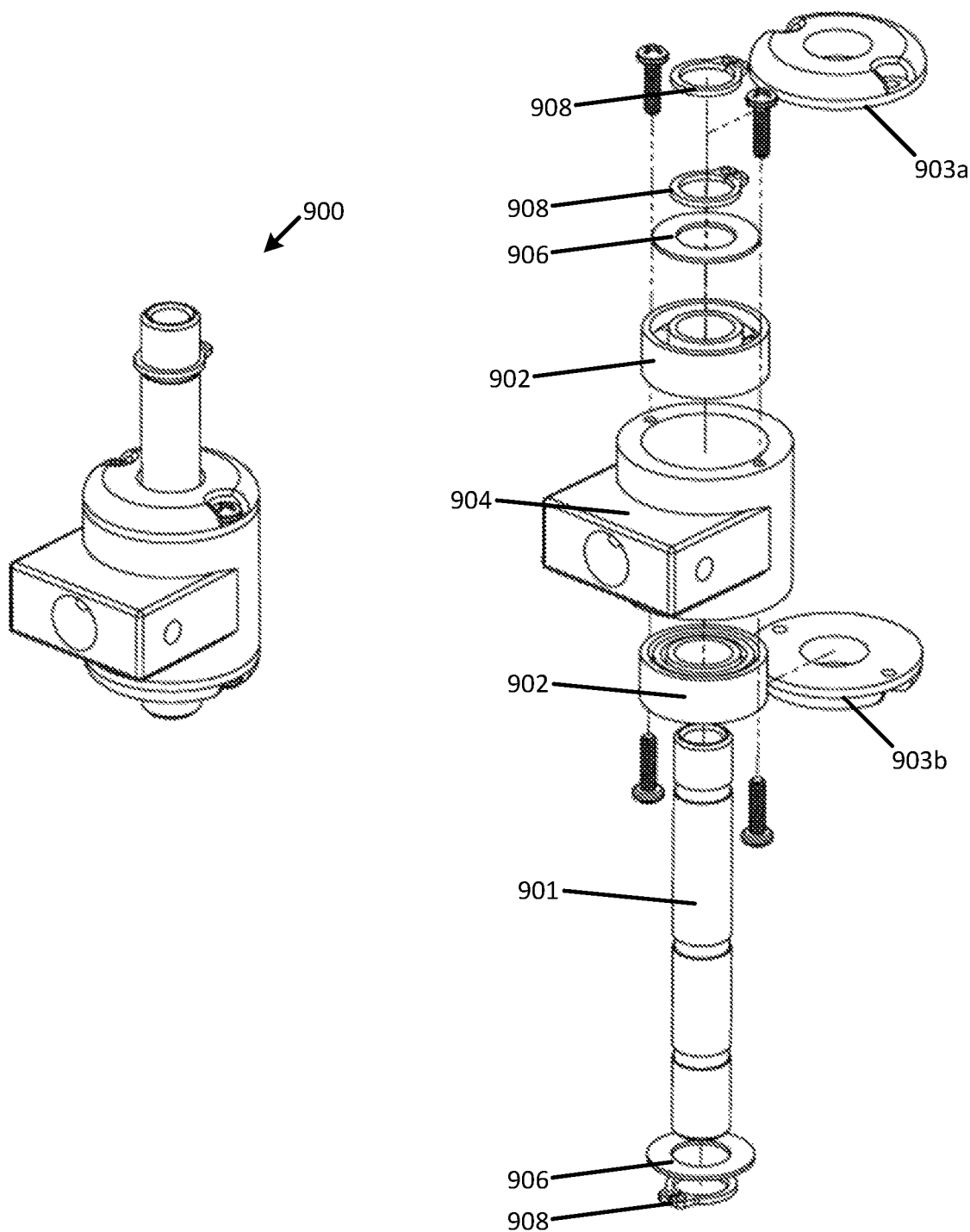
FIG. 9A shows a front perspective view of a bottom Gimbal assembly of the needle and wire instrument of FIG. 1, according to one example embodiment.
FIG. 9B shows an exploded front perspective view of the bottom Gimbal assembly of FIG. 9A.

Referring now to FIGS. 9A and 9B, illustrated therein are perspective and exploded perspective views of the bottom Gimbal assembly 900. The Gimbal assembly 900 is a pivoted support that provides for rotation of an object, i.e. center rod 901, about a single axis. The bottom Gimbal assembly 900 includes two sets of ball bearings 902, each positioned on either side of a Gimbal bracket 904. One or more washers and/or retaining rings 906 and 908, respectively, are on each side of bracket 904. Upper and lower Gimbal caps 903a and 903b provide upper and lower housings, respectively, for the components of ball bearings, washers and retaining rings of the gimbal assembly 900. As previously described, the Gimbal bracket 904 is for coupling the tool assembly 400 and the second bracket 128.

The ball bearings 902 and the washers 906 provide for the center rod 901 to rotate freely while remaining in place without wobble during rotation. Thus, the retaining rings 908 are used as well as a pressure-fit clearance between the ball bearings 902 and machined aluminum support parts (e.g. Gimbal bracket 904). In some embodiments, two ball bearings 902 are included in the bottom Gimbal assembly 900 to reduce wobble of center rod 901. In this embodiment, the ball bearings can also be located with a pressure-fit clearance between them and the bottom bracket 128 for the same reason as with the Gimbal assembly 900.

In some embodiments, ball bearings 902 are all-metal ball bearings. In other embodiments, ball bearings 902 are Igus ball bearings. In some embodiments, the ball bearings 902 are sized between 10 and 15 mm. In some embodiments, 12 mm sized ball bearings are used. In other embodiments, the ball bearings 902 are 13 mm sized ball bearings. Other sizes may be used for the ball bearings for other embodiments, which may use different tools.

Figure 10:
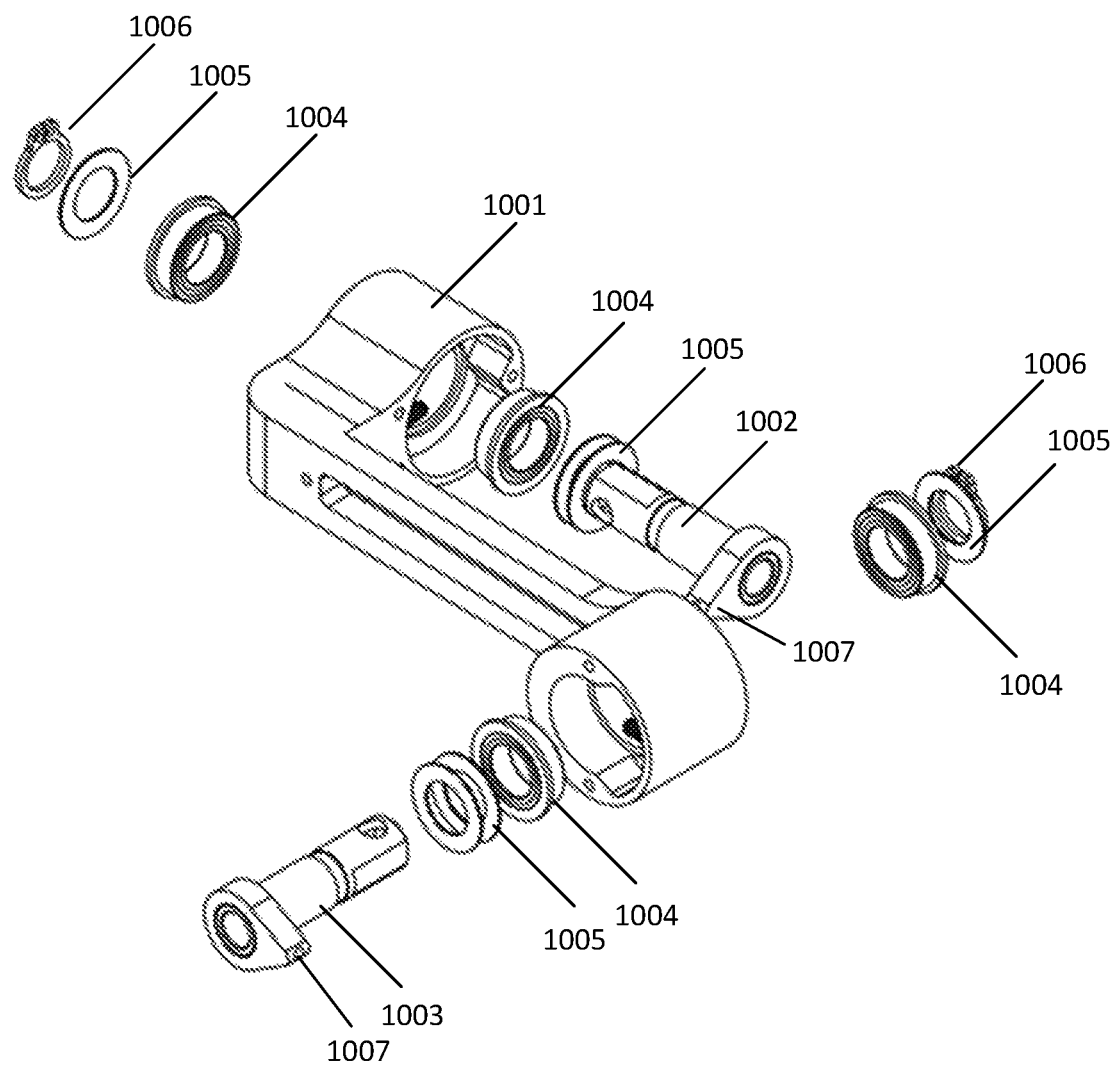
FIG. 10 shows an exploded side perspective view of a bracket assembly of FIG. 3, according to one example embodiment.

Referring to FIG. 10, illustrated therein is a perspective view of a bracket assembly 1000, which is an example embodiment of the first bracket 126 and the second bracket 128 shown in FIGS. 2A and 2B. In FIG. 10, bracket assembly 1000 includes a bracket housing 1001 made out of aluminum or another lightweight but sturdy material. Bracket assembly 1000 also includes a first bracket assembly shaft 1002 that includes a limiter 1007. Limiter 1007 is shown as being threaded through one or more washers 1005 and one or more ball bearings 1004 to inhibit lateral movement relative to the housing 1001 while providing for free rotation within a given angle space. Complete rotation is prevented through the interaction between the limiter 1007 on the first bracket assembly shaft 1002 and the bracket housing 1001 in order to prevent gimbal lock. A second bracket assembly shaft 1003 including a limiter 1007 likewise passes through one or more washers 1005 and one or more ball bearings 1004 in order to prevent lateral movement while allowing free rotation within the given angle space. Bracket assembly 1000 is used to connect to the needle and wire instrument 140 (as seen in FIGS. 2A and 2B) with a bracket shaft such as the first bracket shaft 127a and the second bracket shaft 127b shown in FIG. 3. The interaction between the limiter 1007 and the bracket housing 1001 serves a similar function of preventing full rotation in order to prevent gimbal lock, undue wire stress and other unwanted detrimental conditions. The ball bearings 1004 may be of the same type as ball bearings 902, the washers 1005 may be of the same type as washers 906, and the retaining rings 1006 may be of the same type as rings 908, each described above.

Figure 11:
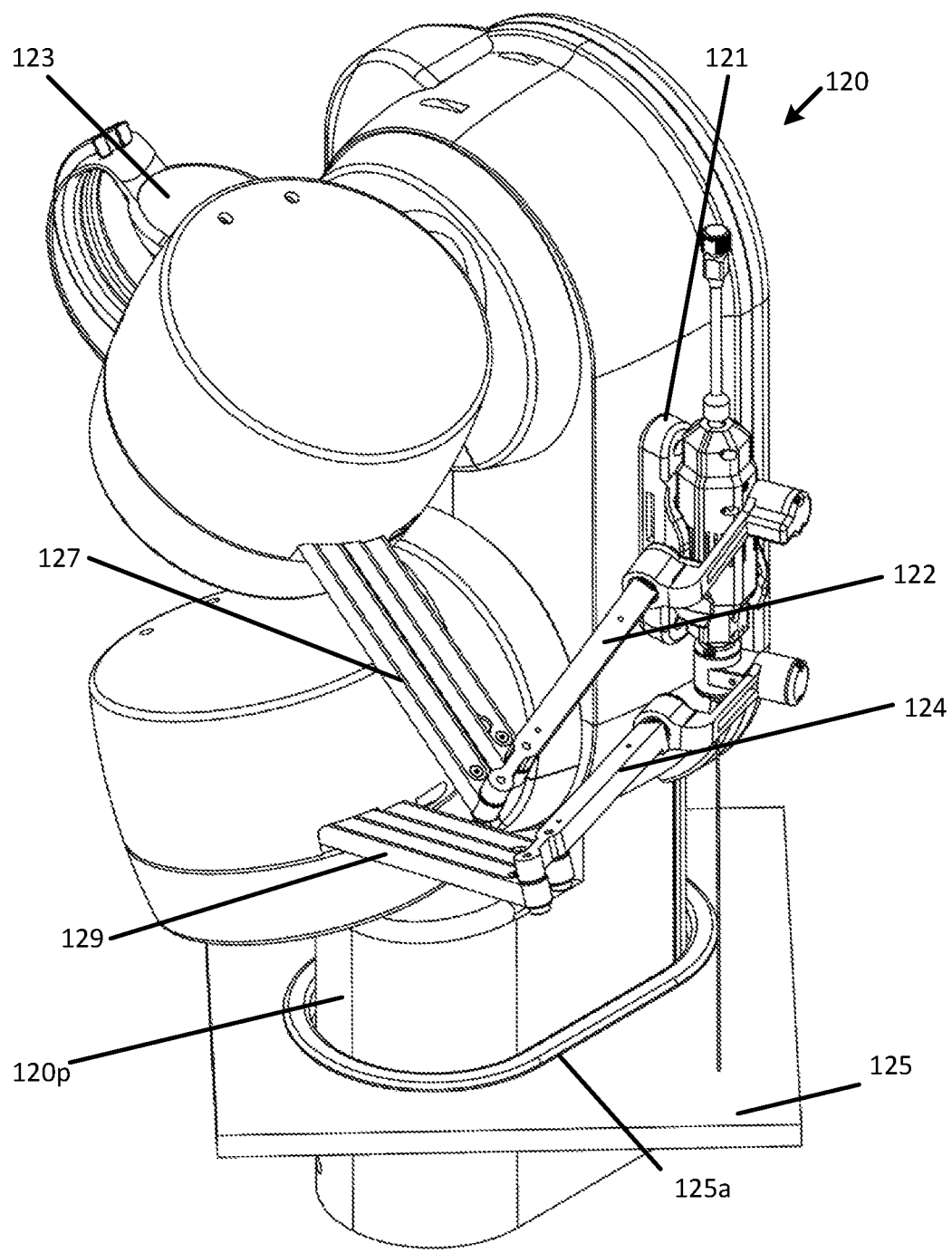
FIG. 11 shows a left perspective view of the haptics assembly of the virtual reality surgical system of FIG. 1 showing the robotic arms of the VR surgical system holding the needle and wire instrument at a mounted position, according to one example embodiment.
Figure 12:
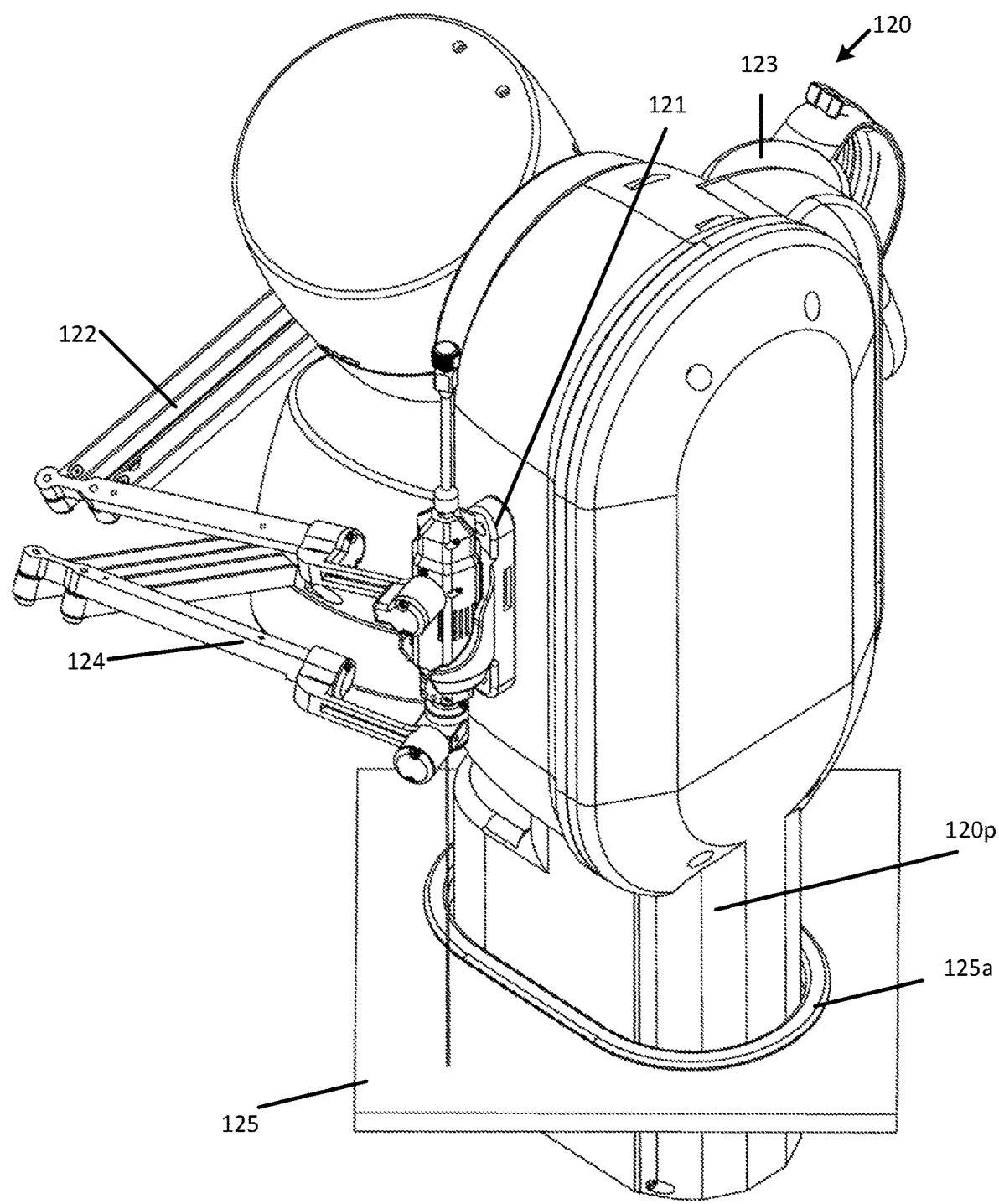
FIG. 12 shows a front perspective view of the haptics assembly of FIG. 11 showing the robotic arms of the VR surgical system holding the needle and wire instrument at the mounted position.
Figure 13:
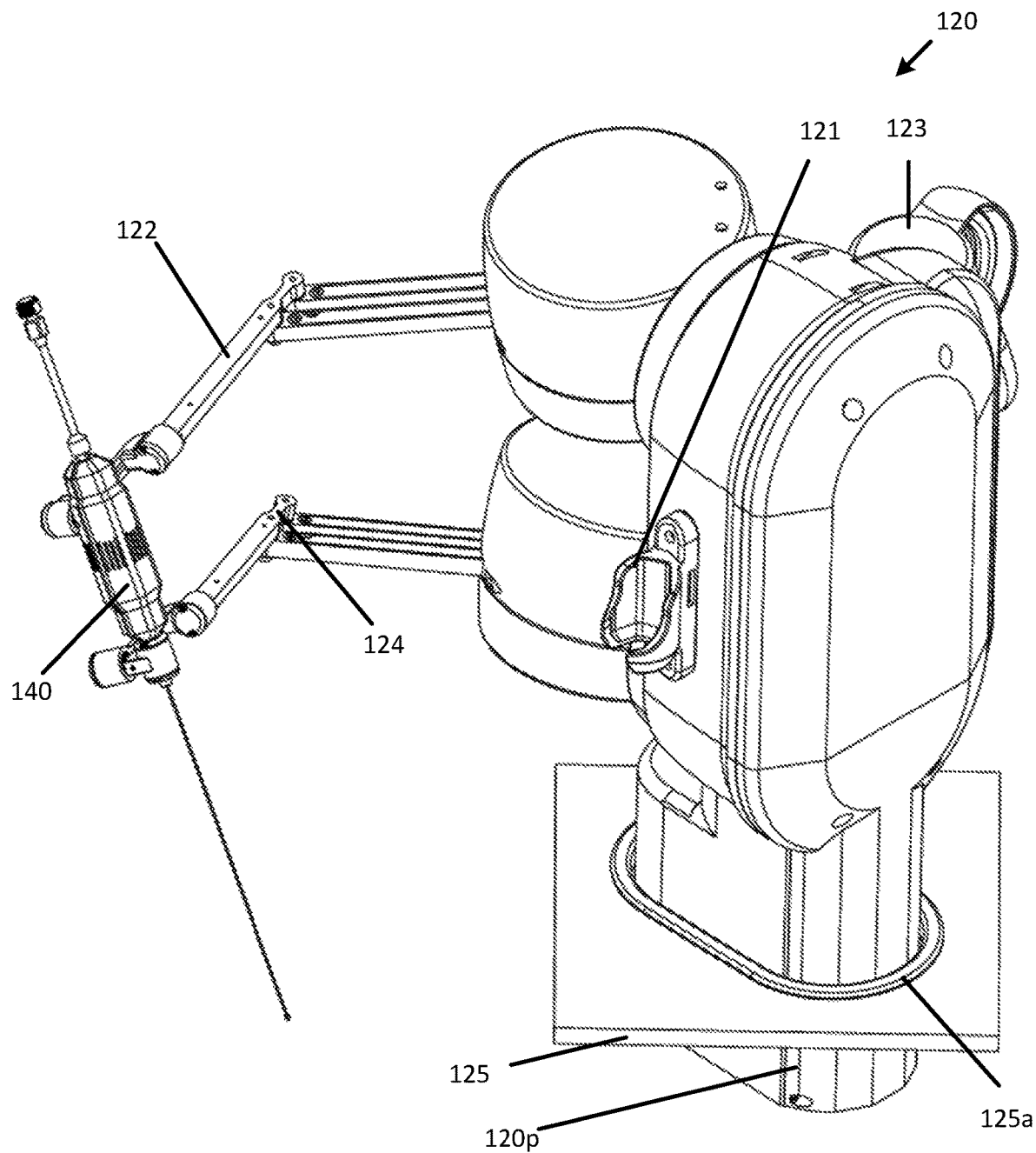
FIG. 13 shows a front perspective view of the haptics assembly of FIG. 11 showing the robotic arms of the VR surgical system holding the needle and wire instrument at a second operational position.

Referring now to FIGS. 11 to 13, illustrated therein is haptic arm assembly 120 according to an example embodiment. As described above, haptic arm assembly 120 includes at least one computing unit (not shown) in communication with the instrument 140, the sensor system 130 and the robotic arms 122, 124. A VR tracker 123 is mounted to the haptic arm assembly 120 to locate the position of the haptic arm assembly 120 in VR space.

The position of the wire assembly 700 and the needle assembly 800 begins in a "home position" when the tool 140 is positioned in a holster 121 as shown in FIGS. 11 and 12. It should be noted that the exact position of the holster as shown in the figures is for reference only, and may be placed above, below or further to the side depending on the necessary working space for the simulated surgery. In some embodiments the holster is positioned along the side of the case as shown in FIGS. 11 and 12, while in others it may be positioned further up to allow the user more working space.

Thereafter, the position and orientation of the wire assembly 700 and the needle assembly 800 can be tracked with reference to the home position while the user is moving the tool 140 to different positions, an example of which is shown in FIG. 13.

The haptic arm assembly 120 is mounted on a post 120p which is positioned within an aperture 125a that is located on the upper surface 125 of the medical cart. It should be noted that the aperture is oriented at an angle with respect to a front face 111f of the medical cart 111 such that the ends of the robotic arms 122 and 124 that hold the tool 140 are oriented towards the user as the user stands in front of the medical cart 111. This is to provide the user with a working area of sufficient size to maximum volume of operation for the user while simultaneously preventing the arms 122 and 124 from adversely interfering with the user's arms during either left or right handed operation.

Figure 14A:
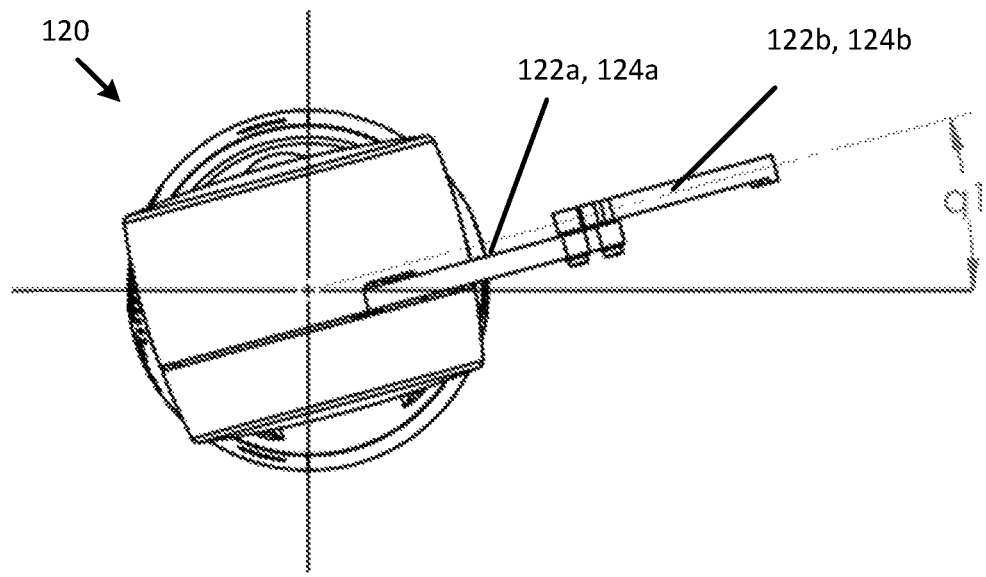
FIGS. 14A-14B show left and top views of the haptic assembly of FIG. 11 showing angles q1, q2 and q3 of the robotic arms of the VR surgical system.
Figure 14B:
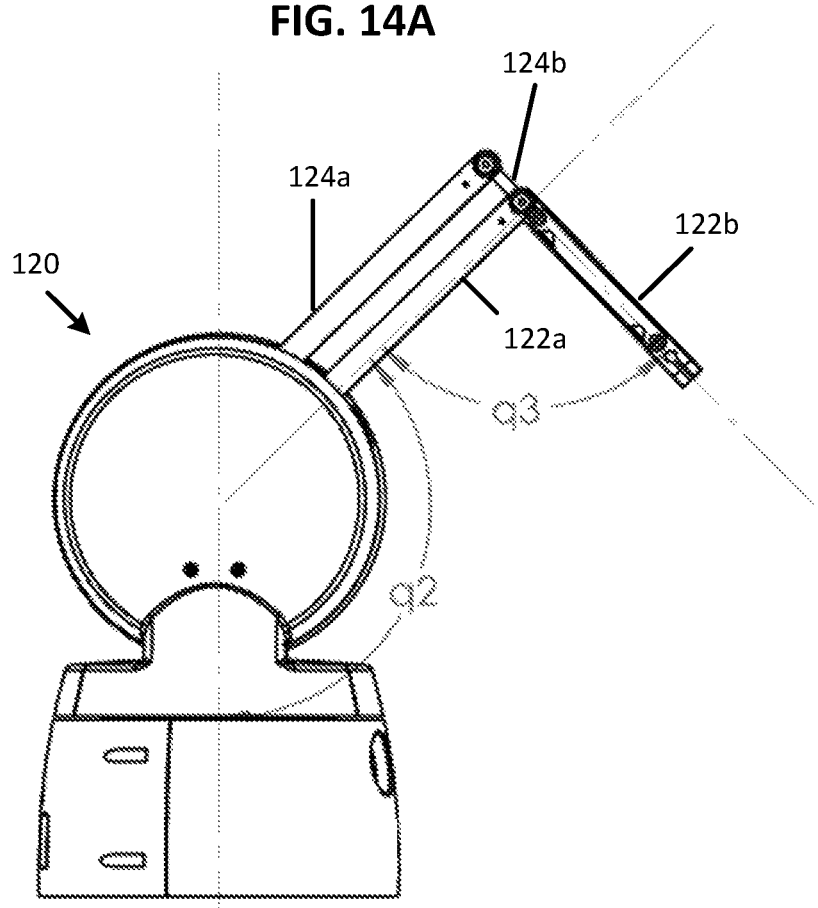

Referring now to FIGS. 14A and 14B illustrated therein are front and top views of the haptic arm assembly 120. FIG. 14A shows an angle of rotation q1 between a plane that includes the robotic arms 122, 124 and a horizontal plane bisecting the haptic arm assembly 120. FIG. 14B shows an angle of rotation q2 between a first portion 122a, 124a of the robotic arms 122, 124 relative to a vertical plane bisecting the haptic arm assembly 120 and an angle of rotation q3 between first portions 122a, 124a of the robotic arms 122, 124 and second portions 122b, 124b of the robotic arms 122, 124. According to some embodiments, haptic arm assembly 120 has a maximum angle of rotation q1 of about 180 degrees, a maximum angle of rotation q2 of about 140 degrees and a maximum angle of rotation q3 of about 100 degrees. In some embodiments, the maximum angle of rotation q1 of about 180 degrees is between angles of about −90 degrees and 90 degrees relative to the angle q1 shown on FIG. 14A, the maximum angle of rotation q2 of about 140 degrees is between angles of about 90 degrees and 230 degrees relative to the angle q2 shown in FIG. 14A, and the maximum angle of rotation q3 of about 140 degrees is between angles of about 40 degrees and 140 degrees relative to the angle q3 shown in FIG. 14A.

Figure 15:
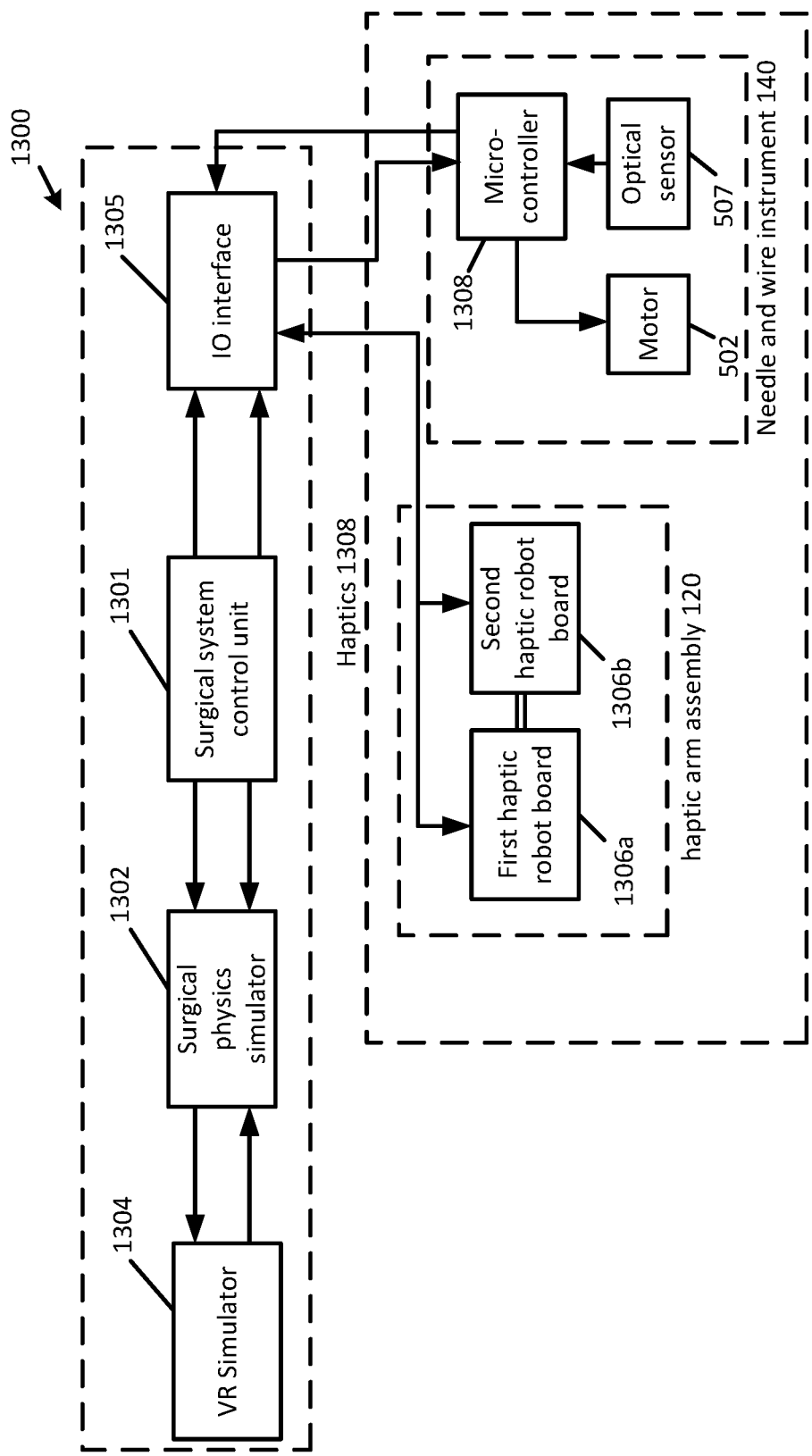
FIG. 15 shows a block diagram of an example embodiment of a system architecture for implementing the electrical and software components for the virtual reality surgical simulation system of FIG. 1.

Referring now to FIG. 15, illustrated therein is a block diagram of an example embodiment of a system architecture 1300 for implementing the electrical and software components for the VR surgical system 100. The haptics system 1300 comprises a surgical system control unit 1301, a surgical physics simulator 1302, a VR simulator (e.g. the Unity VR engine) 1304, haptic robot boards 1306a and 1306b for the robotic arms 122 and 214, respectively, and a micro-controller 1308 (e.g. Arduino) for conveying position of the needle tool 400 (e.g. of the wire assembly 700 and the needle assembly 800) to the user inside of VR. The haptics 1310 of the system 1300 include the electrical elements for the haptics arm assembly 120 and the elements for the needle and wire instrument 140. In this example embodiment, the haptics arm assembly 120 includes the haptic robot boards 1306a and 1306b, as well as various actuators and sensors for the physical robotic arms. The electrical elements of the needle and wire instrument 140 include the micro-controller 1308, the optical sensor 507 and the motor 502. Rotation angles q1, q2 and q3 may be limited based on the type of robotic arms 122, 124 used (e.g. robotic arms 122, 124 were purchased from Entact Robotics Inc., Toronto, ON).

It should be noted that there are several computing units that can be used in the system 1300 including a computing unit for each robotic arm 122 and 124 on the haptic robotic boards 1306a and 1306b, respectively, a computing unit for the wire and tool instrument 140 (i.e. micro-controller 1308), and one or more computing units for the VR simulator 1304, the surgical physics simulator 1302 and the surgical system control unit. The surgical system control unit 1301 is used to control the overall operation of the VR surgical system 100. These computing units can be implemented using one or more micro-controllers, processors, video graphics chips, Application Specific Integrated Circuits and/or other hardware that can provide sufficient processing power for the particular tasks that are to be implemented and may have RAM and/or ROM memory components or be coupled to such memory devices.

In some embodiments, the VR simulator 1304 and the surgical physics simulator 1302 can be executed using the same computing unit (e.g. a computer) at the same time using the same processor (e.g. video card). Alternatively, in some embodiments the VR simulator 1304 and the surgical physics simulator 1302 can be executed on dedicated processors (e.g. different video cards) or even on separate processing units (e.g. different computers) depending on the required computational complexity of either process. Examples of implementations of the VR simulator 1304 and the surgical physics simulator 1302 are provided in the description related to FIG. 16B.

In some embodiments, a computing unit that executes the VR simulator 1304 and the surgery physics simulator 1302 is configured to: generate the virtual environment and output an image of the virtual environment to the display 112, the virtual environment including a model of a patient anatomy and a model of the instrument 140. These models may be constructed from real patient data on a case by case basis, meaning that based on the surgery case you select, the models will be different or these models can be generic models made for the specific surgery being simulated. Alternatively, in at least one embodiment, the operator can be provided with an option to upload patient specific data from a data store (not shown) and complete the simulation using the patient-specific data. The computing unit can receive orientation information of the needle assembly 800 from the instrument 140 and position information of the needle assembly 800 from the sensor system and determine a needle assembly 800 location in the virtual environment. The computing unit can also receive the position information of the wire assembly 700 from the instrument 140 and determine a wire assembly location in the virtual environment. The computing unit can then perform collision detection to determine when there is a collision between either or both of the wire assembly 700 and the needle assembly 800 and at least one aspect of patient anatomy. When the computing unit detects a collision between the wire assembly model and at least one aspect of the patient anatomy within the physics simulation, the computing unit can transmit a signal to cause the instrument 140 to provide a force haptic feedback to the user. The collision detection can be implemented using the surgical physics simulator 1302 which will have a collision-detection algorithm. Furthermore, when the computing unit detects a collision between the needle assembly 800 and at least one aspect of the patient anatomy, the computing unit can transmit a signal to cause one or both of the robotic arms 122, 124 to provide a different kind of force haptic feedback.

Separation of the VR simulator 1304 and the surgical physics simulator 1302 may provide for the replacement of either of these software modules without needing to modify the other simulator, other than possibly modifying a plugin or application programming interface (API) to have these simulators communicate with one another. In addition, separation of the VR simulator 1304 and the surgical physics simulator 1302 may provide for running these software modules on two different pieces of hardware, such as two different video cards, which may be advantageous in cases where the computational complexity of one of the simulators starts to detrimentally impact the operation of the other simulator when performing certain surgical simulations under certain operational conditions.

In one embodiment, the user interacts with the needle and wire instrument 140 which has a rigid body and is coupled via brackets 126, 128 to robotic arms 122, 124. The PCBs housed in the needle and wire instrument 120 contain sensors that provide position information of the wire assembly 700, as previously described, to the surgical physics simulator 1302 via the microcontroller 1308. The needle and wire instrument 140 also contains sensors that provide the position information of the needle assembly 800 with respect to its axis to the haptic robot boards (e.g. 1306a and 1306b). The robotic arms 122, 124 contain sensors that provide the rotation and position information of the needle assembly 800 to the haptic robot boards (e.g. 1306a and 1306b). The surgical physics simulator 1302 utilizes the position of the needle assembly 800 and/or the wire assembly 700 to simulate the surgery in virtual space, which includes determining any forces and motion that occur in VR space as a result of the user interacting with the VR surgical system 100. The determined VR motion is then sent to the VR simulator 1304 which updates the virtual operation in the VR OR and displays the virtual operation to the VR headset 132. The surgical physics simulator 1302 also sends force feedback data based on the determined virtual forces and virtual motion to the micro-controller 1308 and the haptic robot boards 1306a and 1306b which utilize the attached haptics devices (such as the wire's VCM 502a and the rotary motors within the robotic arms 122, 124) to apply the necessary forces to the instrument 140 as haptic feedback to the user. The surgical physical simulator 1302 uses objects in a physics simulation that have contact points and surfaces, and when the needle object with a contact point on the tip comes in contact with a harder surface like skin or an organ, the surgical physical simulator 1302 will recognize this and determine the resulting tactile forces accordingly.

More specifically, in terms of the overall control of the wire 704, the haptic feedback and position information is controlled by the surgical physics simulator 1302. Once an initialization of the position of the wire 704 is determined, the optical sensor 507 detects lateral and/or rotational movement of the wire 704 and translates this movement to a two dimensional movement vector. The two dimensional vector is sent to the micro-controller 1308 which updates the position data indicating the position of the wire 704 based on the net movement experienced by it (as informed by the optical sensor 507) and the last known position. When the surgical physics simulator 1302 polls the micro controller 1308 through the IO interface 1305 for the position data, the micro-controller 1308 can then provide the position data for the last known position of the wire 704. The surgical physics simulator 1302 can then decide what exactly is happening (i.e. the recent movement) to the wire 704 within the virtual surgery, and provide any necessary data (positional, graphical, or otherwise) to the VR simulator 1304 so that it can then display what the wire is doing in virtual space for the user to see on the display 112 and/or the VR headset 132. The friction force that the wire 704 may experience depending on the user's physical actions is calculated by the surgical physics simulator 1302 and sent to the microcontroller 1308, which then sends a control signal to adjust the power provided by the VCM 502a. The change in power provided by the VCM 502a then changes the actual friction force that the wire 704 experiences according to the calculations by the surgical physics simulator 1302. In some embodiments, the flow of data along the path shown in FIG. 15 is completed over 100 times per second so as to provide minimal lag between the user moving the wire 704, and the VR simulation responding to the movement.

Figure 16A:
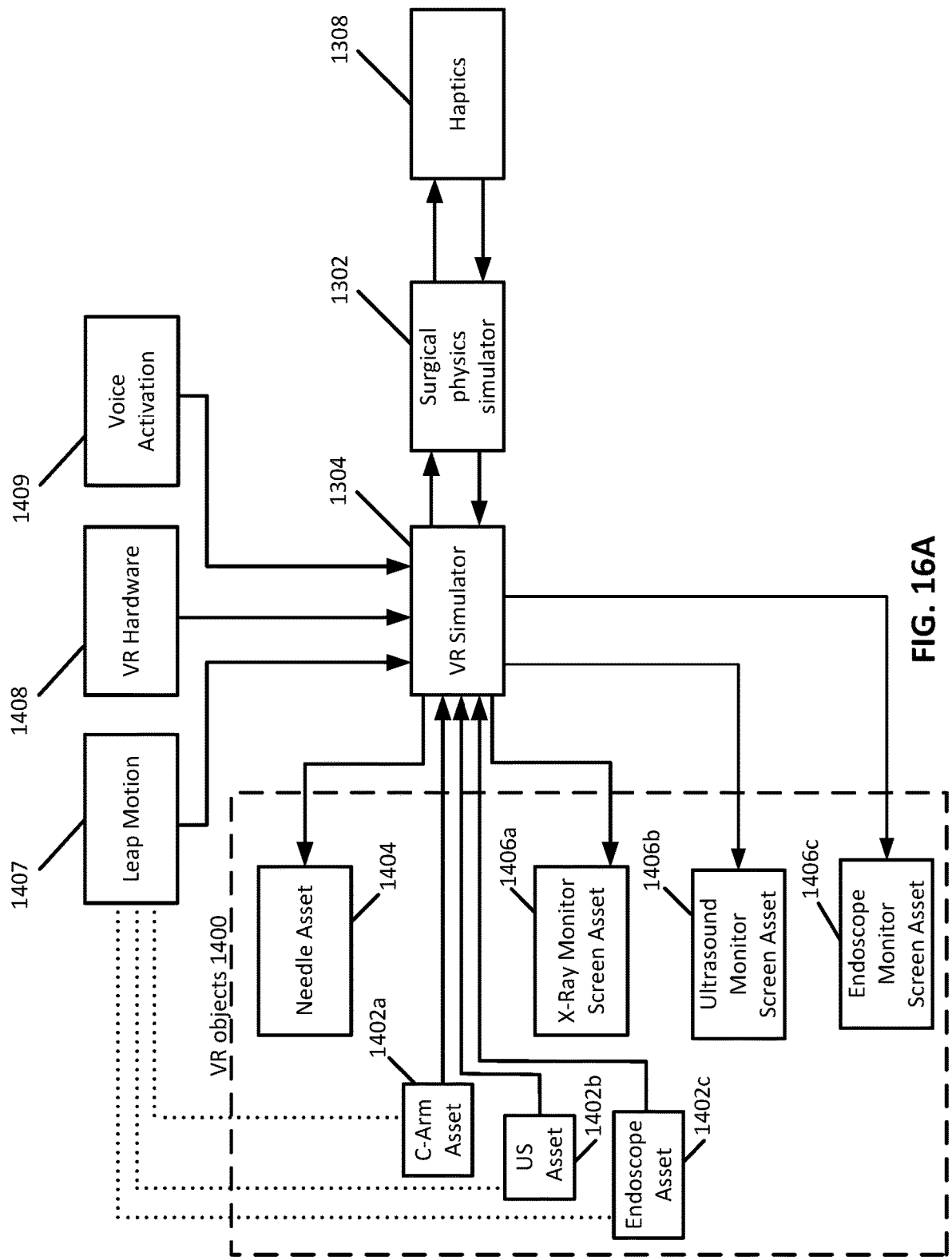
FIG. 16A shows a block diagram of an example embodiment of the interaction between various VR objects for determining and displaying updates in the VR OR based on the user interaction with the VR surgical system and providing haptics feedback to the user.

Referring now to FIG. 16A, shown therein is a schematic diagram showing an example embodiment of the interaction between various VR objects 1400 for determining and displaying updates in the VR OR based on the user interaction with the VR surgical system and providing haptics feedback to the user. The VR objects 1400 include a C-arm asset 1402a, an Ultrasound (US) asset 1402b, an endoscope asset 1402c, a needle asset 1404, an X-ray monitor screen asset 1406a, an ultrasound monitor screen asset 1406b and an endoscope monitor screen asset 1406c. It should be noted that the C-arm asset 1402a is used to obtain virtual data for the X-ray monitor screen asset 1406a, the US asset 1402b is used to obtain virtual data for the US monitor screen asset 1406b, and the endoscope asset 1402c is used to obtain virtual data for the endoscope monitor screen asset 1406c. In some embodiments, there may be at least one of the: (a) the C-arm asset 1402a and the X-ray monitor screen asset 1406a, (b) the US asset 1402b and the US monitor screen asset 1406b, and (c) the endoscope asset 1402c and the endoscope monitor screen asset 1406c.

These assets shown in FIG. 16A are VR objects that are virtual representations of the corresponding physical objects in the virtual world—i.e. in the VR OR. The user can interact with the virtual objects 1400 by providing inputs through various means. These inputs may result in new positional data for any of the virtual objects 1400 and the new positional data is provided to the surgical physics simulator 1302 to determine resulting motion for these virtual objects and forces that may result due to the motion. These forces are then conveyed to the user via the haptics 1308 and the motion may also be displayed on the VR headset 132 and/or the display 112.

For example, the user can move the virtual C-Arm asset 1402a to a new position. This is advantageous since the C-Arm 1402a can be used to take continuous X-ray images (when the surgeon wants them) and display the X-ray images on the X-ray screen monitor within the VR OR. Based on the position and rotation of the C-Arm asset 1402a, the surgeon can get different X-ray alignment which is important in order to be able to insert the needle to the necessary depth (and not overshoot the target). In a similar manner, the user can move the virtual US asset 1402*b* and the endoscope asset 1402*c* as was described for the virtual C-Arm asset 1402*a*.

The user can interact with the C-Arm asset 1402*a* through various software tools such as a leap motion module 1407 and/or voice commands through a voice activation module 1409. The leap motion module 1407 may be provided with movement data that is sensed by the sensors 130. The voice activation module 1409 may be provided with voice control data that is obtained from a microphone that receives vocal commands from a user and the voice control data can be incorporated into the VR surgical system 100. Other alternatives for interaction with the C-Arm asset 1402*a* within the VR reality environment may include VR hardware 1408 such as foot pedals, keyboard shortcuts, touchscreen, or the like. In a similar manner, the user can interact with the virtual US asset 1402*b* and the endoscope asset 1402*c* as was described for the virtual C-Arm asset 1402*a*.

The surgical physics simulator 1302 sends the tool position data and/or visual representations of the surgery to the VR simulator 1304. The visual representations include but are not limited to at least one of 2-dimensional x-ray views, 2-dimensional endoscope views, 2-dimensional ultrasound views and 3D representations of the simulation. The 3D representation may be used to show the user the current state of the simulated surgery (i.e. virtual surgery), while at least one of the x-ray view, the ultrasound view and the endoscope view may be displayed within the VR OR on corresponding virtual screens that the user may use to help guide the virtual surgery. For example, the tool position data stream can be used by the VR simulator 1304 to control an animation (i.e. visualization and movement) of the instrument 140 in a virtual environment (i.e. the VR OR). A second animation can be used by the VR simulator 1304 to make the wire 704 appear as a cylinder that is concentric and protrudes from the top end of the instrument 140 in the virtual environment. As another example, a myopic view of the simulated surgery showing a close up view of an area of the patient anatomy where the simulated surgery is occurring may be provided. The VR headset 132 may generate a view for the user wearing the VR headset 132 from two points at once to simulate a person seeing with two eyes. The close up view of an area of patient anatomy may be generated via selecting appropriate visual models from within the surgical physics simulator 1302 and displaying it within the VR simulator 1304.

For example, a tool tip (e.g. needle assembly 800) is attached to the main haptics device (i.e. the tool assembly 400) and is the object that is tracked using the surgical physics simulator 1302 and shown in the VR OR. Within the VR OR, the tool may be shown as a part of the x-ray view, and/or full 3D models. The tool assembly 400 is the haptics device that provides sensing and feedback for the inner tool (e.g. wire assembly 700) that inserts through the tool tip (e.g. needle 800) and feedback for the tool-tip (e.g. needle assembly 800). It should be noted that the inner tool (wire assembly 700) can represent almost any tool that can be inserted into the tool tip (e.g. needle 800) as the tool tip can be interchangeable in at least some embodiments to provide surgical simulations using different tools (an example of which is shown in FIGS. 17A-18B).

At least a portion of the inner tool (e.g. wire 704 of wire assembly 700) inserts into the tool tip (e.g. needle 800) and passes through the tool tip (e.g. needle 800) into the haptics device 140. Inside the haptics device 140, the movement of the portion of the inner tool (e.g. wire 704 of wire assembly 700) is measured and any forces necessary for providing haptic feedback to the user are applied. The inner tool can be wire 704, graspers, or another secondary tool that can be inserted into the haptics device 140. In some embodiments, additional haptics beyond the wire interface haptics described here may be included in the haptics device 140. For instance, haptics may be added that provide a user with a sensation of graspers grasping an object. In these embodiments, additional haptics may be added to inner tool (e.g. wire assembly 700) and connected to the surgical system control unit 1301 through some appropriate communication means outside of the haptics device, such as through a USB interface, for example.

To map real world tools to the Virtual Reality Operating Room (VR OR), the VR tracker 123 (e.g. an Oculus VR touch controller, a Vive™ puck, another third party tracking hardware, or similar) is mounted on the back of the robotic arms 122, 124. The VR tracker 123 locates the robot tower 120*p* and pinpoints the robotic arms 122, 124 in space, which configures how the virtual bed/tool is placed when the user opens the VR OR. The user is wearing the VR headset 132, whose position is known relative to the sensors 130 on the base 110 of the medical cart 111. The VR headset 132 also includes a sensor (such as a Leap Motion sensor), which records dual channel video from roughly the position of the user's eyes. Data from the two video channels can then be used with the leap motion software to calculate the most likely position of the user's hands and fingers. This data is then sent to the VR simulator 1304 which displays the user's hands in the VR environment (i.e. the VR OR) thereby allowing the user to see a virtual representation of their hands. Using their virtual hands in the VR OR, the user can grab a virtual tool, such as the virtual C-arm, to move the virtual tool around in the VR OR. For the C-arm, the user can also command the C-arm with voice control to move and change the angle of the C-arm in the VR OR. The ability of the VR surgical system 100 to receive voice commands to control the C-arm is advantageous since in actual surgeries the surgeon typically tells a nurse to position the C-arm at a given angle and the nurse then moves the C-arm. The position of the C-arm is provided to the surgical physics simulator 1302 which generates an x-ray image that is then sent to the VR simulator 1304 which can then show the updated C-arm position to the user via a virtual X-ray monitor, the VR headset 132 and/or the display 112. The same can be done with any other virtual tool that can be included in the surgery simulation without the need for haptic feedback.

Figure 16B:
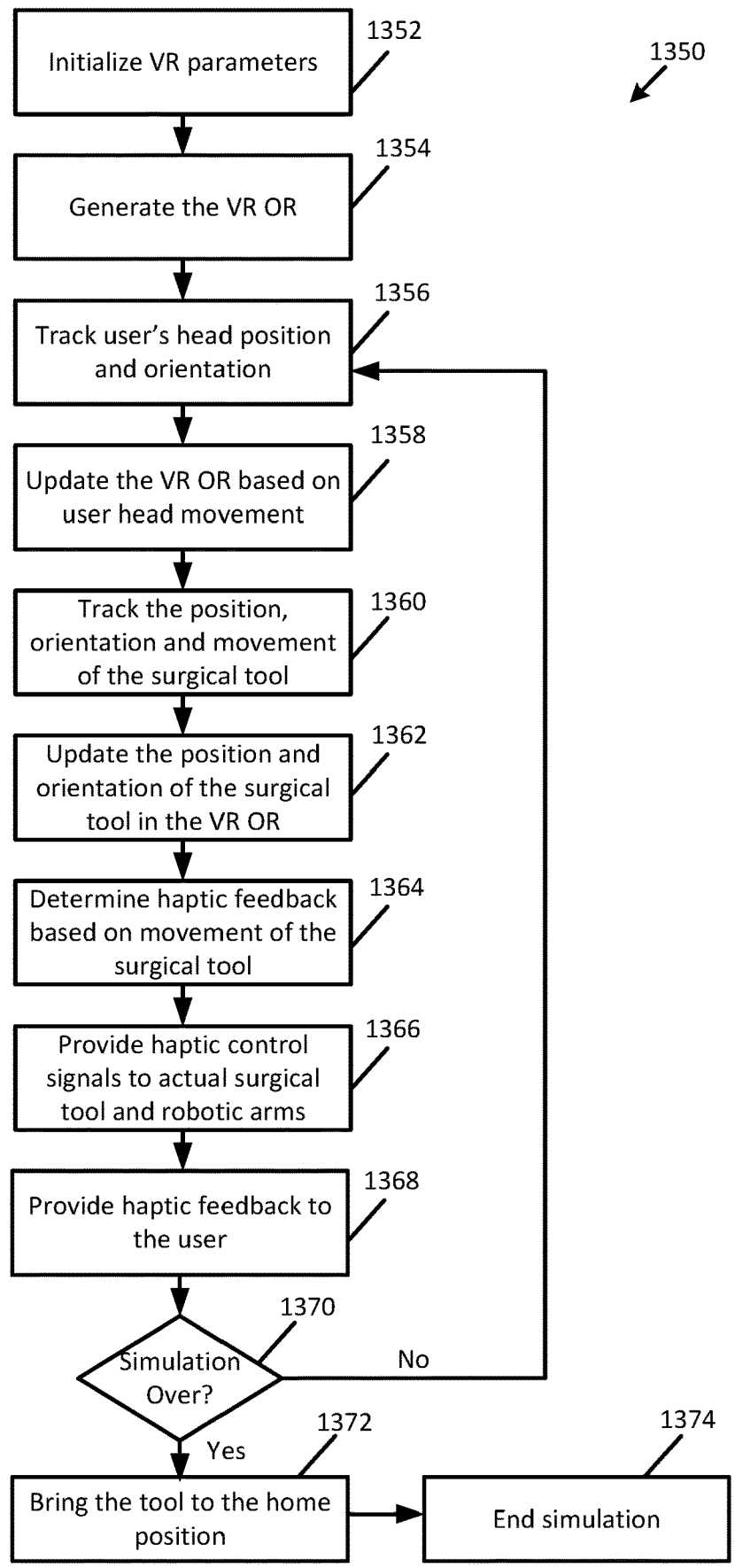
FIG. 16B shows a flow chart diagram of an example embodiment of a virtual reality surgical simulation method that can be used with the VR surgical system of FIG. 1.

Referring now to FIG. 16B, illustrated therein is a process flow diagram of an example embodiment of a virtual reality surgical simulation method 1350 that can be used with the VR surgical system 100.

At act 1352, VR parameters of the for the virtual/simulated surgery are initialized. This may include a user selecting a surgery to perform, patient options, selecting VR OR characteristics, surgical tool type and surgical tool characteristics.

At act 1354, the VR OR is generated. In some embodiments, the VR OR is generated using the VR simulator 1304 (i.e. via a Unity VR engine; e.g. Unity version: 2017.4.2f2) using the current model geometry given by the surgical physics simulator 1302 and applying any necessary post processing onto them (e.g.: texturing, bump-mapping, etc.). In general, most of the visual information necessary for the user to see what is going on is transferred from the surgical physics simulator 1302 to the VR simulator 1304. For example, in the case of a kidney surgery, the surface data of a kidney model is transferred (i.e. a plurality of sets of three points and a normal) which is then used to generate the exact same model within the VR simulator 1304 which allows the user to see the kidney) The Unity VR engine may include a Virtual Reality Tool Kit (VRTK) plugin. The Unity VR engine can be used to implement the VR simulator 1304. The surgery physics simulator 1302 may be implemented using a Simulation Open Framework Architecture (SOFA), which is a French open source physics simulator (e.g. V17.12).

At act 1356, sensors 130 track the user's head position and orientation. At act 1358, as previously described, the head position and orientation of the user is continuously provided to the VR simulator 1304 which updates the Field of View (FOV) of the OR VR based on the user head movement.

At act 1360, data from the VR tracker 123, data from the sensors in the haptics assembly 120 and data from the sensors in the wire position sensor assembly 500 are used to track the position, orientation and movement of the instrument 140. The position, orientation and movement data of the instrument 140 is continuously provided to (e.g. updated) in the VR OR (at act 1362) via the micro-controller 1308 and the surgical physics simulator 1302.

At act 1364, haptic feedback is determined based on movement of the surgical instrument 140. The haptic feedback determination results from collision detection between either or both of the position of the wire assembly 700 and the needle assembly 800 and at least one aspect of patient anatomy in the VR. When the surgical physics simulator 1302 detects a collision between the needle assembly 800 and at least one aspect of the patient anatomy, the surgical physics simulator 1302 can transmit a signal to cause one or both of the robotic arms 122, 124 to provide force haptic feedback at act 1366. When the surgical physics simulator 1302 detects a collision between the wire assembly 700 and at least one aspect of the patient anatomy, the surgical physics simulator 1302 can transmit a signal to cause the instrument 140 to provide a force haptic feedback to the user at act 1368.

Following the provision of haptic feedback, the method 1350 determines if the simulation is over at act 1370. If the simulation is over, the instrument 140 is returned to the home position at act 1372 and the simulation ends at act 1374. If the simulation is not over, the method 1350 returns to act 1356 and continues to track the movement of various objects and provide haptic feedback depending on the user's actions.

In one example embodiment, a percutaneous nephrolithotomy (PCNL) can be simulated using the various components of the surgical VR system 100. In this embodiment, to perform the procedure, a user punctures a patient with the needle and then twists off a handle to remove the center of the needle while holding the cannula in place, and then inserts the wire through the cannula into the body. Using the VR surgical system 100, a wire 704 is connected to the handle of the center needle 702 even though there is no actual physical center needle. While the user sees in the VR OR that they are pulling out the center needle from the cannula, in reality they are pulling the wire 704 out of the needle 800 up until the maximum limit at which point either the clip 706 prevents the wire from being fully removed from the needle 800, or force is applied via the VCM 502*a* within the tool assembly 400 to make the user realize he or she should stop pulling. At the same time an animation of the wire being inserted into the needle is shown in the VR OR environment following which the user can physically push the wire 704 back down the needle 800. During the actual surgery this step is done to place the wire down into the kidney and further down into the ureter, which the simulation simulates through the wire-needle haptic system combined with the VR OR. Throughout the entire simulation the user can see the movement of the needle and wire within the patient through the x-ray view displayed on a virtual screen inside the VR OR, simulating how a surgeon is only be able to see what is going on within the patient during these steps of the surgery only through the x-ray view within the operating room.

Referring now to FIGS. 17A, 17B, 18A and 18B, illustrated therein are additional components for coupling to the tool instrument 140 to simulate different types of medical procedures using a different medical instrument. For instance, a nephroscope handle 1502 of a nephroscope 1500, shown in FIG. 17A, can be coupled to the instrument 140 previously described. In one embodiment, the nephroscope handle 1502 can replace the needle assembly 800 and screws onto one end of the instrument 140 via a wire stopper 1504. In other embodiments, other coupling elements besides screws can be used including but not limited to clamps, magnets or snap-ins.

In this example embodiment, the nephroscope 1500 comprises a rod 1506 that is used in place of the wire assembly 700. The movement of the rod 1506 is similar to the wire 704 as was previously described, where the optical sensor 507 reads the translation and rotation of the rod 1506 and provides position information to the microcontroller 1308 and the surgical physics simulator 1302. The surgical physics simulator 1302 in turn feeds back the signal to the VCM 502*a*, which applies a force on the rod 1506 and thus the grasper handle 1508. In one embodiment, the grasper rod 1506 attaches directly to the wire assembly 700; however, in other embodiments the wire assembly 700 can be removed entirely along with the needle tool tip 800 before the nephroscope tool tip 1502 is attached to the main haptics tool assembly 140. The rod 1506 is then inserted through the nephroscope handle 1502 (which acts as a tool tip) and into the main haptics tool assembly 140, its endpoint interacting directly with the optical sensor 507 and VCM 502*a* so as to read the movement of the graspers and provide the force feedback. Just as the needle assembly 800 was rigidly attached to the housing 401, so is the nephroscope handle 1502. Accordingly, in this embodiment, there are five directions of force feedback acting on the nephroscope handle 1502, coming from the two robotic arms 122, 124.

Figure 19:
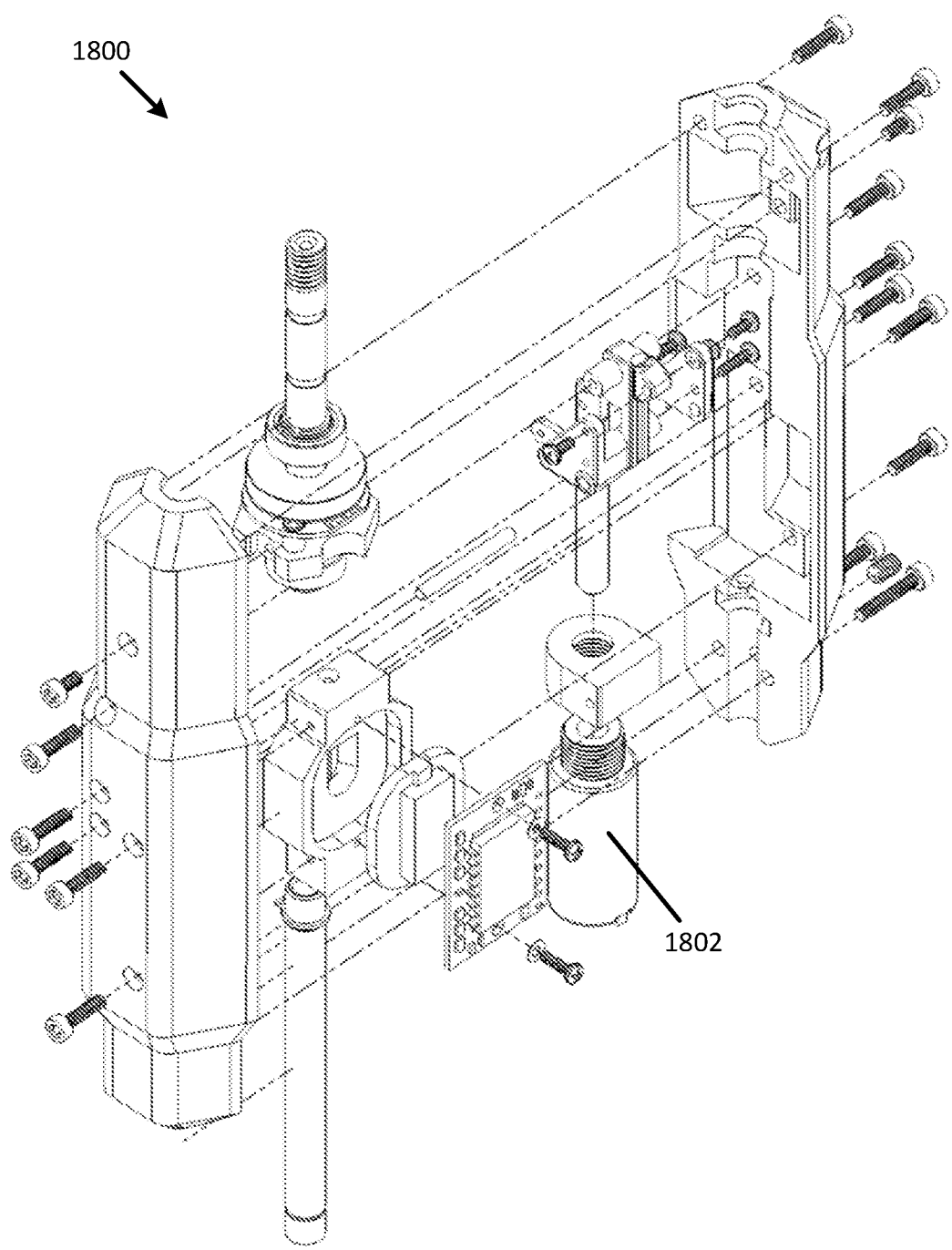
FIG. 19 shows an exploded front perspective view of an instrument assembly of a needle and wire instrument, according to another example embodiment.

Referring now to FIG. 19, illustrated therein is an alternate embodiment of a tool assembly of the instrument 140. In this embodiment, tool assembly 1800 includes a solenoid 1802 in place of VCM 502*a*. In this embodiment, calibration of tool assembly 1800 can be done as the solenoid 1802 may provide variable amounts of force to the wire. For example, the tool 1800 can be calibrated for each type (e.g. diameter) of wire that is used.

In the embodiments described herein, the terms "elongated member force feedback assembly" can refer to an assembly of parts that provide haptic force feedback to an elongated member such as but not limited to a wire (e.g. wire 704). Other examples of elongated members may include but are not limited to a rod, a cable, a bar, a stick or the like. The term "elongated member sensor assembly" can refer to an assembly of parts that sense a position of an elongated member such as but not limited to a wire (e.g. wire 704).

The term "surgical tool assembly" can refer to an assembly of parts that form a surgical tool such as but not limited to a needle (e.g. needle assembly 800). Other examples of surgical tool assemblies may include a nephroscope (see. FIGS. 17A to 18B) or the like.

The term "moveable elements" can refer to elements such as but not limited to eccentric presses 508a and 508b that apply a frictional force onto the elongated member.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

The invention claimed is:

1. An instrument for simulating surgical procedures in a virtual environment with haptic feedback, the instrument comprising:
   a tool assembly having an outer wall defining a cavity of the tool assembly;
   first and second brackets each having first shafts that are rotatably coupled at first and second end regions of the tool assembly and second shafts that are rotatably coupled to first and second robotic arms, allowing a user to move the instrument;
   a surgical tool assembly coupled to an end portion of the tool assembly and having an elongated member that extends within the tool assembly;
   an elongated member position sensor assembly housed within the cavity and configured to provide position information of a position of the elongated member of the instrument to a computing unit; and
   an elongated member force feedback assembly housed within the cavity and coupled to the elongated member, the elongated member force feedback assembly being configured to receive a control signal from the computing unit causing the elongated member force feedback assembly to apply a frictional force on the elongated member to provide haptic feedback to the user of the instrument when the computing unit detects a collision between at least one aspect of a patient anatomy and at least one of the tool assembly and the elongated member in the virtual environment.

2. The instrument of claim 1 further comprising a tool rotation sensor assembly located at the tool assembly and coupled with the surgical tool assembly and configured to provide orientation information of an orientation of the surgical tool assembly to the computing unit.

3. The instrument of claim 2, wherein the tool rotation sensor assembly includes a code wheel having lines arranged thereon and a PCB configured to measure rotations of the code wheel based on the lines and to transmit the measurements the orientation of the surgical tool assembly.

4. The instrument of claim 1, wherein the elongated member position sensor assembly comprises an optical sensor to detect lateral and axial movement of the elongated member.

5. The instrument of claim 1, wherein the elongated member force feedback assembly includes moveable elements that move in response to the control signal to apply friction on the elongated member to provide the haptic feedback.

6. The instrument of claim 5, wherein the moveable elements comprise eccentric presses.

7. The instrument of claim 6, wherein the two eccentric presses press on opposed sides of the elongated member to provide the frictional haptic feedback.

8. The instrument of claim 5, wherein the elongated member force feedback assembly includes a motor coupled to the moveable elements and configured to direct the moveable elements to apply the friction on the elongated member to provide the haptic feedback.

9. The instrument of claim 1, further comprising a Gimbal assembly located at a bottom end portion of the tool assembly and coupled to the first shaft of the second bracket, the Gimbal assembly allowing for the tool assembly to be rotated about a longitudinal axis of the tool assembly.

10. The instrument of claim 1, wherein each of the first and second brackets include at least one rotary limiter along at least one of the first and second shafts, the first and second shafts each being coupled to the tool assembly and one of the robotic arms.

11. The instrument of claim 1, wherein the surgical tool assembly comprises a needle assembly and a wire assembly that is separate from the needle assembly longitudinally extends through the needle assembly and the tool assembly, is longitudinally moveable with respect to the needle member and the tool assembly, and comprises a wire that is the elongated member.

12. The instrument of claim 11, wherein the needle assembly is coupled to the tool rotation sensor assembly at an upper end portion of the tool assembly.

13. The instrument of claim 1, wherein the surgical tool assembly comprises a nephroscope having a nephroscope handle and a nephroscope grasper that is separate from the nephroscope handle and has a rod that longitudinally extends through the nephroscope handle and the tool assembly, is longitudinally moveable with respect to the nephroscope handle and the tool assembly, and acts as the elongated member.

14. The instrument of claim 13, wherein the nephroscope handle is coupled to the tool rotation sensor assembly at an upper end portion of the tool assembly.

15. A system for simulating surgical procedures in a virtual environment with haptic feedback, the system comprising:
   a Virtual Reality (VR) headset that is worn by a user;
   an instrument having a tool assembly, a surgical tool assembly coupled to and extending from an end of the tool assembly and an elongated member that is moveable through the tool assembly and the surgical tool assembly, the instrument being configured to:
      provide orientation information of an orientation of the surgical tool assembly;
      provide positional information of a position of the elongated member; and
      provide frictional force haptic feedback to the user in response to the position of the elongated member;
   a sensor system configured to detect a position of at least a portion of the surgical tool assembly and provide position information of the position of the portion of the surgical tool assembly;
   at least one robotic arm coupled to the tool assembly, the robotic arm configured to provide applied force haptic feedback to the user in response to the position of the surgical tool assembly; and
   a computing unit in communication with the instrument, the sensor system and the at least one robotic arm, the computing unit being configured to:
      generate the virtual environment and output an image of the virtual environment to the VR headset display, the virtual environment including a model of a patient anatomy and a model of the surgical tool assembly;

receive the orientation and position information of the surgical tool assembly and the elongated member and determine a surgical tool assembly location and orientation an elongated member location and orientation in the virtual environment;

perform a physical simulation of the interaction between at least one of the surgical tool assembly and the elongated member and at least one aspect of the patient anatomy;

transmit a first control signal to cause the instrument to provide the frictional force haptic feedback to the elongated member based on the physical simulation of the interaction; and transmit a second control signal to cause the at least one robotic arm to provide the applied force haptic feedback to the surgical tool assembly.

16. The system of claim 15, wherein:
the tool assembly includes an outer wall defining a cavity of the tool assembly;
the surgical tool assembly is coupled to an end portion of the tool assembly and includes the elongated member that extends within the tool assembly; and
the instrument further comprises:
   first and second brackets each having first shafts that are rotatably coupled at first and second end regions of the tool assembly and second shafts that are rotatably coupled to first and second robotic arms, allowing the user to move the instrument;
   an elongated member position sensor assembly housed within the cavity and configured to provide the position information of the position of the elongated member of the instrument to the computing unit; and
   an elongated member force feedback assembly housed within the cavity and coupled to the elongated member, the elongated member force feedback assembly being configured to receive the first control signal from the computing unit causing the elongated member force feedback assembly to apply a frictional force on the elongated member to provide the frictional force haptic feedback to the user of the instrument when the computing unit detects a collision between the at least one aspect of the patient anatomy and at least one of the tool assembly and the elongated member in the virtual environment.

17. The system of claim 15, wherein the computing unit is further configured to:
   generate an image of a C-arm in the virtual environment that is used to obtain virtual X-ray images showing the virtual interaction of the instrument with the patient anatomy;
   provide the user with the virtual X-ray images through voice commands or inputs provided to VR hardware by the user; and
   display the virtual X-ray images in the virtual environment on a virtual X-ray monitor.

18. The system of claim 17, further comprising a display that is communicatively coupled with the computing unit for displaying a given virtual X-ray image or a portion of the virtual environment.

19. The system of claim 18, wherein the instrument, the at least one robotic arm and the display are mounted on a cart.

20. The system claim 15, wherein the computing unit is further configured to:
   generate an image of an ultrasound device in the virtual environment that is used to obtain virtual ultrasound images showing the virtual interaction of the instrument with the patient anatomy;
   provide the user with the virtual ultrasound images through voice commands or inputs provided to VR hardware by the user; and
   display the virtual ultrasound images in the virtual environment on a virtual ultrasound monitor.

21. The system of claim 15, wherein the computing unit is further configured to:
   generate an image of an endoscope device in the virtual environment that is used to obtain virtual endoscope images showing the virtual interaction of the instrument with the patient anatomy;
   provide the user with the virtual endoscope images through voice commands or inputs provided to VR hardware by the user; and
   display the virtual endoscope images in the virtual environment on a virtual endoscope monitor.

22. A method for simulating a medical procedure on a patient anatomy in a virtual reality environment and providing haptic feedback to a user who interacts with a physical instrument, the method being executed on at least one computing unit, the method comprising:
   executing, by a Virtual Reality (VR) simulator, a simulation of the medical procedure;
   receiving instrument location information corresponding to a location of at least a portion of the physical instrument;
   determining, by a surgical physics simulator, interaction between a virtual representation of the physical instrument and the patient anatomy;
   generating haptic control signals based on the determined interaction;
   rendering, by the VR simulator, a virtual reality operating room scene that corresponds to the medical procedure and indicates the interaction between the virtual representation of the physical instrument and the patient anatomy;
   displaying, by at least one of a virtual reality headset and a physical display, at least a portion of the rendered virtual reality operating room scene to the user; and
   providing haptic feedback to the physical instrument using the haptic control signals.

23. The method of claim 22, wherein the method further comprises allowing virtual X-ray images to be taken showing the interaction between the instrument and the patient anatomy in the virtual environment and displaying the X-ray image to the user via the virtual reality headset and/or the physical display.

24. The method of claim 22, wherein the at least a portion of the rendered virtual reality operating room scene comprises a myopic view of the simulated surgery showing a close up view of an area of the patient anatomy where the simulated surgery is occurring.

25. A system for simulating surgical procedures on a patient anatomy in a virtual environment with haptic feedback, the system comprising:
   a Virtual Reality (VR) headset that is wearable by a user;
   a display;
   an instrument having a tool assembly, a surgical tool assembly coupled to and extending from an end of the tool assembly and an elongated member that is moveable through the tool assembly and the surgical tool assembly, the instrument being moveable by the user and being configured to provide orientation and position information of the surgical tool assembly and the elongated member and provide haptic feedback to the user in response to a haptics control signal;

at least one robotic arm coupled to the tool assembly and configured to provide haptic feedback to the user; and a computing unit in communication with the instrument, the at least one robotic arm and the display, the computing unit being configured to:
  receive the orientation and position information of the surgical tool assembly and elongated member;
  generate a virtual representation of the surgical tool assembly and the elongated member in the virtual environment based on the orientation and position information;
  determine an interaction between at least two of the virtual representation of the surgical tool assembly, the elongated member and the patient anatomy;
  generate the haptics control signal based on the interaction; and
  display an image of at least a portion of the surgical tool assembly, the elongated member, and the patient anatomy in the virtual environment on at least one of the VR headset and the display.

* * * * *